(12) United States Patent
Kamb et al.

(10) Patent No.: US 6,582,899 B1
(45) Date of Patent: *Jun. 24, 2003

(54) METHODS FOR IDENTIFYING AGENTS THAT CAUSE A LETHAL PHENOTYPE, AND AGENTS THEREOF

(75) Inventors: Carl Alexander Kamb, Salt Lake City, UT (US); Giordano Michael Caponigro, Salt Lake City, UT (US)

(73) Assignee: Deltagen Proteomics, Inc., Salt Lake City, UT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/504,132

(22) Filed: Feb. 15, 2000

(51) Int. Cl.[7] .............................. C12Q 1/68; G01N 1/30; G01N 38/48
(52) U.S. Cl. .............................. 435/4; 435/6; 435/40.5
(58) Field of Search .............................. 435/4, 6, 40.5

(56) References Cited

FOREIGN PATENT DOCUMENTS

WO    WO 94/25621    * 11/1994

OTHER PUBLICATIONS

Alberts et al, Molecular Biology of the Cell (text), 1989, p. 408.*

Luban and Goff, current Opinion in Biotechnology, 1995, vol. 6, pp. 59–64.*

Freshney, Culture of Animal Cells, (monograph), 1994, pp. 232.*

Piazza et al, Cancer Research, 1995, vol. 55, pp. 3110–3116.*

Clarke et al, Cytometry, 2000, vol. 39, pp. 141–150.*

Caponigro et al, PNAS, 1998, vol. 95, pp. 7508–7513.*

Fukazawa et al, Oncogene, 1999, vol. 18, pp. 2189–2199.*

* cited by examiner

*Primary Examiner*—Anthony C. Caputa
*Assistant Examiner*—Karen A. Canella
(74) *Attorney, Agent, or Firm*—Marshall, Gerstein & Borun

(57) ABSTRACT

The present invention is directed to methods for performing negative selection assays leading to the identification of cytostatic or cytotoxic agents that cause a lethal phenotype. The invention is useful also for evaluation of conditional cytotoxicity and cell-specific cytotoxicity.

30 Claims, 26 Drawing Sheets

Figure 2
Adherent
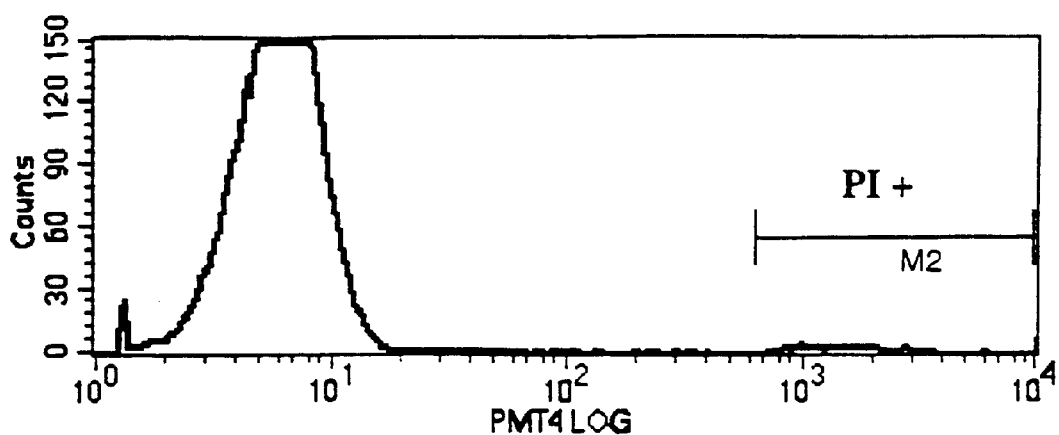
Floaters
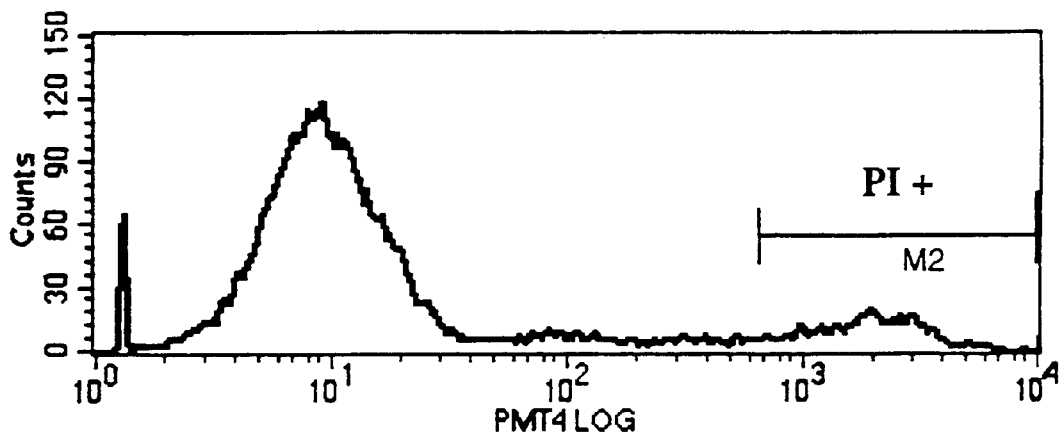

Construction of GFP with Internal XhoI-EcoRI-BamHI Restriction Sites

Figure 7
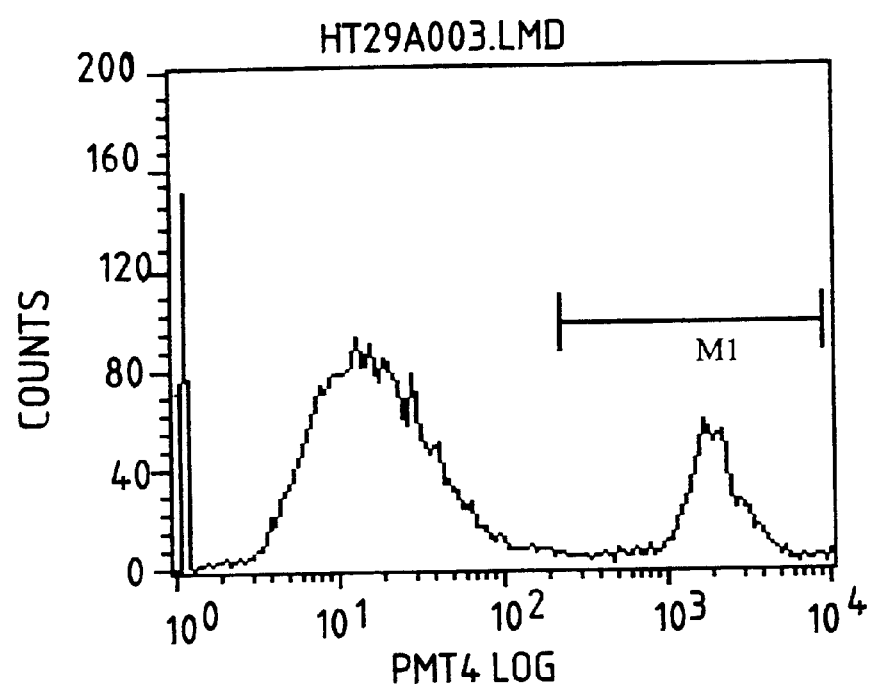
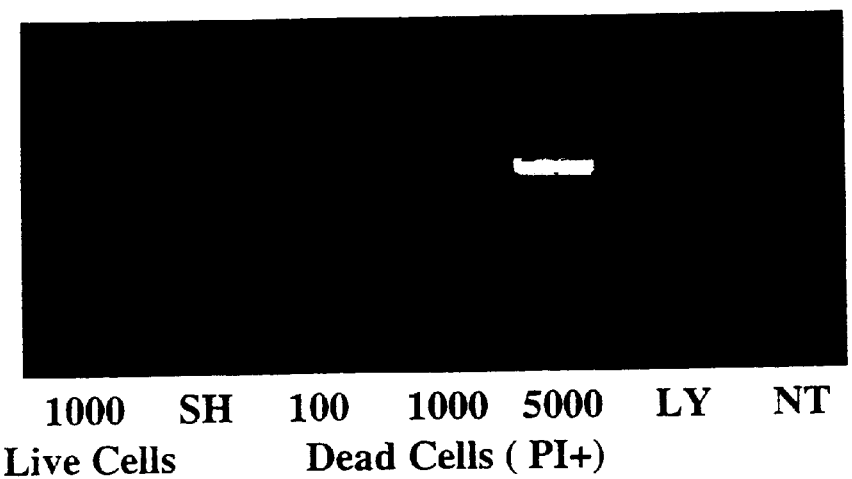
1000　　SH　　100　　1000　　5000　　LY　　NT
Live Cells　　　　Dead Cells ( PI+)

A) Sequence of Full Length BID and BID Clones #1 and #2

MDCEVNNGSSLRDECITNLLVFGFLQSCSDNSFRRELDALGHELPVLAPQWEGDELQTDGNRSSHSRLGRIEADSESQEDIIR

NIARHLAQVGDSMDRSIPPGLVNGLALQLRNTSRSEEDRNRDLATALEQLLQAYPRDMEKEKTMLVLALLLAKKVASHTP

SLLRDVFHTVNFNONLRTYVRSLARNGMD

B) CLONE 0113
PQLLRQARSPAFIY

C) CLONE 0195
PEILSRSHLLAGQTLIGVVAMVVEAEGEEDPWAVEAMEVVAVVVVAEEDFPVEVVAVEDSSELVTGSVLIPPVRI

D) CLONE 0328
XXAVAWLGSTGMTCGAQRLRSLR

E) CLONE 0461
PHSVPAPSILAVRVPEAEWLHPSPSPASDLWLWSPCPCLHPRAPHPPGFTKEGGAVCSSCTQHLGQGGAAADGPREAPGALS
ESPAFQLPKAASGECGKAIIRALAA

Figure 9

Day 5 floater rates

F0 = starting library
F2 = after one collection, one sort
F3 = one collection, two sorts
F4 = one collection, three sorts

US 6,582,899 B1

METHODS FOR IDENTIFYING AGENTS THAT CAUSE A LETHAL PHENOTYPE, AND AGENTS THEREOF

BACKGROUND OF THE INVENTION

Cancer and other diseases involving abnormal or undesired cellular proliferation present a major challenge to the pharmaceutical industry. Desirable therapeutic compounds frequently act on cellular targets to inhibit cellular growth and/or kill unwanted cells. In order to identify such therapeutic compounds efficiently, it is often desirable to identify the cellular targets that are involved in such growth inhibition or cell death. Yet such cellular targets are difficult to identify, because cells exhibiting the desired phenotype disappear from a cell population, and consequently the targets (and the corresponding causative agents) are lost.

In general terms, experiments that identify agents that inhibit cellular growth and/or kill cells are termed "negative selections"—i.e., selections for compounds that exert a cytotoxic or cytostatic effect on a cellular population. Such negative selections are needed for pharmaceutical research relating to a number of areas, including cancer, viral infection and the like. The art to date has not provided efficient, generally applicable methods for conducting negative selections in mammalian cells—i.e., for directly identifying the causative agents and subsequently recovering the targets that interact with such agents to result in growth inhibition or in cell death.

The lack of efficient negative selection protocols is of particular concern in the field of cancer research. Drug discovery for cancer requires identification of therapeutic agents that interact with endogenous cellular targets so as to provide a cytotoxic effect on the diseased or abnormal cell. Preferably, such agents also will act with specificity for the target cell type—i.e., selectively killing unwanted cells, while sparing healthy, normal cells. One method for identifying such valuable therapeutic agents is to first identify an endogenous cellular target involved in that cytotoxic effect, and then use that target as the basis of a screen to identify small molecule modulators that interact with the target. Alternatively, therapeutic agents may be either proteinaceous compounds that interact with an endogenous cellular target or nucleic acids that prevent either the production or function of that target. In such cases, it is desirable to directly recover the agent that caused the desired cellular inhibition or death.

In the case of cell death, the modulated target may in some instances be involved in an apoptotic pathway, and in other instances, may be involved in necrosis. In general terms, apoptosis is the process of normal, programmed cell death in an organism, while necrosis is a less specific, regulated response that lacks many biochemical features associated with apoptosis. Many clinical manifestations of cancer are believed to represent a malfunction in this normal apoptotic process—i.e., a failure of normal cell death, leading to uncontrolled proliferation of transformed cancer cells in the body. Thus, the pharmaceutical industry particularly desires to identify agents that will selectively promote the apoptotic process, thereby encouraging death of the unwanted cancerous cells.

Much of the current research for new chemotherapeutic agents focuses largely on identifying new compounds that interact with, or modulate the effect of, proteins that are already known to play a key role in a given disease pathway. One such example is recent work on the role of thymidine kinase in cancer, and the resulting discovery of 5-Fluorouracil and folate analogues. Such techniques, however, are inherently limited by the scope of pre-existing knowledge of such key proteins. To maximize the development of new chemotherapeutic agents for, e.g., cancer, it is preferable to be able to broadly and generally screen for cytotoxic compounds without being so limited to a small pre-existing pool of targets.

Several general methods relate to the identification of dead or dying cells, but lack the ability to directly identify substances that caused the cell death (and, therefore, do not lead to the direct identification of the cellular target that modulates its cytotoxic effect); for example, a variety of staining methods identify necrotic and/or apoptotic cells. Such methods include antibody staining techniques and dye staining techniques such as, e.g., propidium iodide staining. Other assays employ laborious replica plating techniques, whereby duplicate colonies are established and one such colony is exposed to putative cytotoxic agents. When cellular death is observed in the one colony (via its death, or absence from a replica plate), its corresponding duplicate is then subjected to further analysis. However, such replica plating techniques are time-consuming and not suited to high-throughput screening procedures. Moreover, at best the replica plating technique is an approximation, as the actual endogenous cellular materials that are involved in the cell death are lost with the duplicate colony that disappears from the replica plate.

Thus, a need exists for a negative selection technique that is direct (i.e., it is the dead or dying cells themselves that provide the causative agents and corresponding endogenous targets relating to their death). Moreover, a need exists for a negative selection technique that provides rapid, efficient evaluations—i.e., a technique that is suitable for high-throughput screening. The present invention meets these needs.

SUMMARY OF THE INVENTION

The present invention provides methods for performing negative selections. In some embodiments, the negative selections are performed by introducing a genetic library into a population of target cells, collecting a subpopulation of cells that disattach from a culturing surface, and then recovering the genetic material from that subpopulation. In other embodiments, the invention provides methods for obtaining cytotoxic agents that establish a lethal phenotype, wherein a genetic library is introduced into a population of target cells, a subpopulation of cells displaying a lethal phenotype is collected, and genetic material is then recovered from that subpopulation. In variations of these embodiments, cell-specific cytotoxic agents are identified by employing a counterscreening step wherein the genetic material from the subpopulation displaying disattachment and/or the lethal phenotype is introduced into a second, different population of cells, and a second sublibrary of genetic material is obtained from a second subpopulation that does not display disattachment and/or the lethal phenotype.

A variety of particular embodiments exist for each of these basic embodiments. In some particular embodiments, the lethal phenotype of the methodology may be apoptosis, necrosis, or growth arrest. In embodiments in which the lethal phenotype is apoptosis, the property of disattachment from a culturing substrate may be used as a surrogate for apoptosis, thereby providing a technique for enriching the apoptotic cell population. In other particular embodiments, the genetic material may be partially sequenced, or the method steps may be reiterated in a second population of the same cells. The target cells may be mammalian cells, or more particularly primary cells, especially primary cells derived from epithelial or endothelial cells, stem cells, mesenchymal cells, fibroblasts, neuronal cells or hematopoeitic cells. The mammalian cells may also be cancer cells, or more particularly cancer cells that are metastatic or derived from solid tumors. The cancer cells may particularly be derived from breast, colon, lung, melanoma or prostate tissue. In other particular embodiments, the mammalian cells are genetically altered, and more particularly may be immortalized or transformed.

In embodiments that utilize the property of disattachment of target cells from a culturing surface, particular embodiments will feature a low background of spontaneously disattaching cells, which may more particularly be no more than about 10%, or alternatively no more that about 2%. Target cells having such low backgrounds include SW620 and HT29 colon cancer cells, T47D breast cancer cells, and HuVEC cells. In particular embodiments, the disadhering cells are collected over a period of at last about 12 hours. In still other particular embodiments of the basic embodiments, the genetic library is large or even very large(~$10^5$ encoded putative cytotoxic agents).

The invention also encompasses the identification of small organic molecules that induce a lethal phenotype. In some embodiments, organic molecules that displace a proteinaceous cytotoxic agent from an endogenous protein are obtained. In other embodiments, organic molecules having a structure-activity relationship with that proteinaceous cytotoxic agent are identified.

The invention also lends itself to embodiments that screen for conditional cytotoxicity, wherein a genetic library is introduced into a population of target cells, exposing those target cells to a subtoxic threshold dose of a secondary reagent, collecting a subpopulation of cells displaying a lethal phenotype, and recovering genetic material from that subpopulation. Again, in particular embodiments the lethal phenotype may be apoptosis, necrosis or growth arrest. In other particular embodiments, the secondary reagent may be UV, X-ray or neutron radiation, or may be a chemotherapeutic agent, more particularly methotrexate, cisplatin, 5-fluorouracil, colchicines, vinblastine, vincristine, doxyrubicin or taxol. Particular embodiments include cancer cells, more particularly solid tumors, as target cells, counterscreening with a second cytotoxic substance, preconditioning the target cells prior to exposure with, e.g., growth factors, cytokines, chemokines, or activation of oncogenes.

The invention also encompasses compositions of matter, more particularly six representative amino acid sequences, that are obtained by applying the inventive negative selection methods to HT29 colon cancer cells.

BRIEF DESCRIPTION OF THE DRAWINGS

FIG. 2 is a pair of histograms depicting the differential fluorescence patterns of adherent vs. disadhered ("floater") cells stained with propidium iodide.

FIG. 7 is a FACS histogram of PI+ (dead) HT29 cells (gate M1), and a gel showing subsequent PCR amplification of that fraction.

FIG. 9 contains the peptide sequences of six cytotoxic agents isolated from a negative selection in HT29 colon cancer cells. Sequence (A) (SEQ ID NO: 20) depicts two BH3 Interacting Domain Death Agonist (BID) fragments. The full length pro-BID is 195 amino acids long. Pro-BID is cleaved at amino acid 55 (LQTD (SEQ ID NO: 25), gray text) by caspase 8. The thin underline region represents BID clone number 1 (amino acids 33–195). The thick underline region represents clone number 2 (amino acids 76–195). The shaded region "LAQVGDSMD" (SEQ ID NO: 26) (gray) represents the BH3 (Bcl-2 homology) domain. Sequence (B) (SEQ ID NO: 21) is the amino acid sequence of a cytotoxic agent isolated from a clone designated 0113. Sequence (C) (SEQ ID NO: 22) is the amino acid sequence of a cytotoxic agent isolated from a clone designated 0195. Sequence (D) (SEQ ID NO: 23) is the amino acid sequence of a cytotoxic agent isolated from a clone designated 0328 (xx represents unreadable sequence). Sequence (E) (SEQ ID NO: 24) is the partial amino acid sequence of a cytotoxic agent isolated from a clone designated 0461. The cytotoxic agent is estimated to be approximately 230 amino acids in length or greater.

DETAILED DESCRIPTION OF THE PREFERRED EMBODIMENTS

Figure 1:
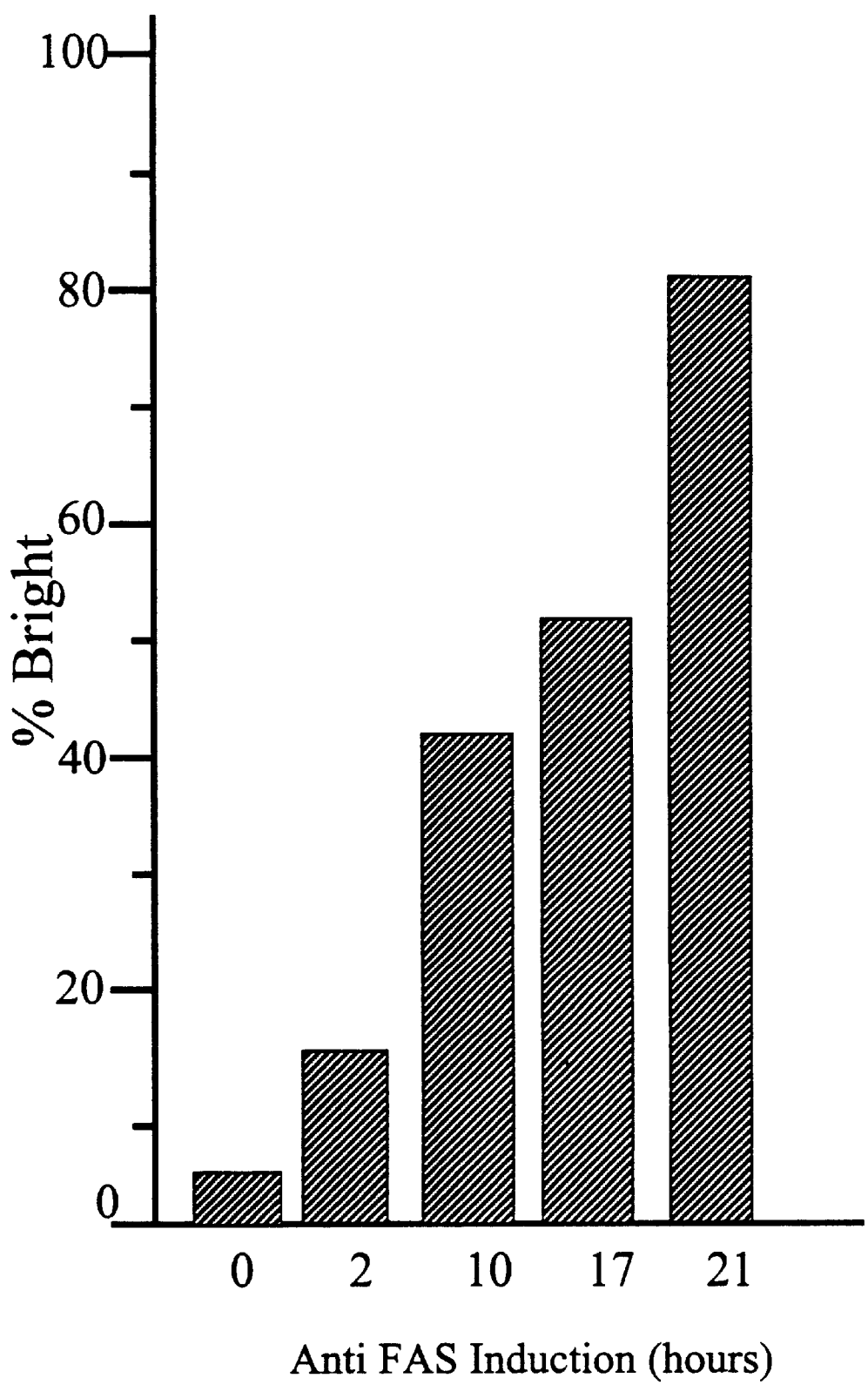
FIG. 1 is a bar graph depicting the results of FACS analysis of Jurkat cells labeled with Apo2.7, in response to induction of apoptosis with the anti-FAS antibody.

Overview of the Invention.

The invention provides a rapid, efficient way of screening for (i) lethal agents or substances that cause or accelerate cellular death of a cell, or for (ii) agents that trigger growth and/or reproductive arrest in a population of cells and, thus, eventually lead to the demise of that population. Both types of agents are referred to herein as "cytotoxic agents," as the end result is the loss of a cell population.

The invention accomplishes this end of efficient screening by providing negative selection assays that first either directly or indirectly selects for a lethal phenotype, and then yields direct recovery of the modulators of endogenous proteins that create that phenotype.

By "negative selection" is meant a procedure designed to identify and isolate cells that are in one of any number of stages of growth arrest and/or cell death—i.e., are evidencing a lethal phenotype. By "lethal phenotype" is meant one or more cellular events that result, directly or indirectly, in death of an individual cell or a cell population.

The lethal phenotype may be the result of any number of physiological events resulting in cell death. As non-limiting examples, the cells may die by an active, pre-programmed pathway such as apoptosis or by a more passive, degenerative means such as necrosis, i.e., as a direct result of creating lethality in individual cells. In other instances, the cells may disappear as an indirect result, e.g., via some form of growth arrest. Such growth arrest may be caused by a variety of mechanisms that block normal cellular development, thereby freezing the cell in a given stage of its cell growth cycle. For example, p16-induced growth arrest halts the cells in the G1 phase of the cell cycle.

Generally, the selection methods of the invention begin by providing a target cell population in which cells displaying a lethal phenotype may be readily recovered. A variety of methods are available for such recovery, many of which involve cell sorting utilizing a fluorescent marker that directly or indirectly identifies dead or dying cells, or even more specifically, distinguishes apoptotic vs. necrotic cells. In other instances, the lethal phenotype may have a surrogate phenotype that provides for ready recovery of the desired target cell subpopulation. As one example, the property of loss of cell adhesion can correlate with cell death, thus providing for simple enrichment and/or selection for cells having the correlative lethal phenotype. As another example, alterations in cellular structure and/or function may be an appropriate surrogate for lethality—e.g., loss of P-glycoprotein overexpression correlates to increased sensitivity to chemotherapeutic drugs in resistant cell lines and, therefore, to increased rates of cell death.

One particular advantage of the invention is the direct recovery of genetic material encoding the cytotoxic agents. By "direct recovery" is meant the recovery of genetic material from the growth arrested and/or dead or dying cell itself (as opposed to indirect methods such as replica plating). Thus, the techniques provide a direct sampling of the nucleic acids that constitute or encode the agents that cause the lethal phenotype. Such direct recovery is advantageous in that the actual, causative genetic material is recovered and preserved for subsequent manipulation and/or analysis, and for re-screening or counterscreening the individual library inserts in another target cell population.

The invention is equally applicable to screening discrete cytotoxic agents, or to libraries of putative cytotoxic agents. In some embodiments, the library to be screened may be a large library (i.e., more than about $1 \times 10^3$ agents), or even a very large library (i.e., more than about $1 \times 10^5$ agents). Although the invention may be used to evaluate an agent with a known or suspected cytotoxic effect, it is equally applicable to screening agents that previously were uncharacterized—i.e., were not known or suspected to exert a cytotoxic effect. In some instances, the agents will be proteinaceous or nucleic acid moieties, while in others, the agents to be screened can be small organic molecules.

The invention is well suited for evaluating the activity of a cytotoxic agent in the presence or absence of other agents (e.g., sensitizers or synergistic reagents). Thus, in some embodiments, the invention may be utilized to evaluate "conditional cytotoxicity," in which one identifies a potentiating agent (e.g., a sensitizer encoded by a genetic library insert) that increases the sensitivity of a cell to a secondary reagent (e.g., a known chemotherapeutic drug or radiation from a variety of sources, including ultraviolet, X-ray and neutron). Thus the potentiating agent enhances the cytotoxicity of the secondary reagent, rendering a normally subtoxic dosage or exposure of that secondary reagent cytotoxic. This approach is of particular interest in evaluating candidate agents for ameliorating multidrug resistance (MDR) in, e.g., cancer cells, thereby making such cells susceptible to standard chemotherapeutic agents such as, e.g., taxol, adriamycin, vinblastine, actinomycin D, methotrexate, cisplatin, 5-fluorouracil, colchicine, vincristine, doxyrubicin and the like.

In still other embodiments, the target cells may presensitized via some agent or that does not itself exert a deleterious effect, for example, by addition of a growth factor. In other instances, the target cells may be presensitized by activating the expression of a gene of interest, for example, an oncogene.

The invention also lends itself to readily identifying agents that act in a "cell-specific" manner. This can be accomplished by conducting a counterscreening step utilizing a second cell type. In such embodiments, the invention may be utilized to identify cytotoxic agents that exert a differential cytotoxic effect, for example by selectively killing a first type of cell, while under similar conditions not exerting a cytotoxic effect on a second cell type. As one specific but non-limiting example, a library encoding putative cytotoxic substances may be screened in a first cell population—e.g., a cancerous cell line such as WM35. Agents that cause a lethal phenotype in those cells are then isolated and screened in a second, corresponding primary cell line. Agents that do not cause a lethal phenotype in the non-cancerous cell line are then isolated and further characterized.

Identification of a Lethal Phenotype

A variety of methods exist for identifying cells having a lethal phenotype. For example, many methods familiar to those of ordinary skill in the art target cellular components such as surface antigens that arise only upon a cell's entry into an apoptotic or necrotic pathway. In other instances, a change in cellular morphology or cellular permeability that characterizes the lethal phenotype is observed—e.g., changes in nuclear membrane integrity or "blebbing" of the cell membrane. A variety of dyes, stains and antibodies are available for such methods, including without limitation the antibody Apo 2.7, propidium iodide, and caspase dyes. When an identification agent is fluorescent, cells displaying a lethal phenotype may readily be isolated from viable cells using a fluorescence activated cell sorter (FACS), and the genetic material recovered from the resulting isolated subpopulation of dead and/or dying cells.

In other instances, a gross morphological or physiological characteristic that is readily detected may be used as a surrogate for the lethal phenotype. In some cell types, lack of cellular adhesion is an excellent surrogate for cell death. Alternatively, the presence or absence of a cellular marker such as a cytoplasmic membrane-associated protein may be monitored.

Target Cells

A wide variety of different cell types are suitable for use as target cells. In general, cells that bear some relation to a known pathology or disease state, or to a known target tissue or cell population, are utilized. In many embodiments, the target cells will be mammalian cells.

In many instances, the disease of interest is cancer. Often the cell type will represent a solid tumor, and metastatic cancer cells are of particular interest. Representative cancer types include, without limitation, breast, colon, prostate and lung tumors, as well as melanoma. Corresponding cell lines include, without limitation, SW620, HT29, DLD1, T47D, WM35 and the like.

In other instances, it may be desired to explore lethal phenotypes in primary cells such as Human Umbilical Vein Endothelial Cells (HuVECs). In general, the invention readily lends itself to screening a variety of primary cell cultures derived from epithelial cells, endothelial cells, stem cells, mesenchymal cells, fibroblasts, neuronal cells and hematopoietic cells. In some instances, the primary cell lines may be used in a counterscreening step to investigate the selectivity of a cytotoxic agent. In other instances, for example in angiogenesis, it may be desired to identify agents that are cytotoxic to the primary cells themselves.

The invention is also applicable to performing negative selections in genetically altered primary cells. As non-limiting examples, the primary cell may be genetically altered so as to immortalize it, using standard techniques familiar to those of ordinary skill in the art. Immortalizing techniques include use of well-known genes such as HPV-E6, HPV-E7, hTERT, activated ras, SV40 large T-Antigen, Epstein-Barr Virus (EBV) BARF1 gene, Human T-Cell Leukemia Virus Type 1 (HTLV-1) TAX (transactivation) gene, and adenovirus E1A. In other instances, the primary cell lines may be transformed by a variety of standard techniques. For example, cells that are lacking one or more known tumor suppressor may be used. Alternatively, a wide variety of transformed or immortalized cell lines are available from ATCC and other such sources.

In many instances, it is also preferable that the target cells have a low background rate for whatever identification characteristic or surrogate characteristic used to select for the lethal phenotype of interest. As one example, in the case of a floater assay for apoptosis, target cells that have (i) low backgrounds of spontaneous dissociation and/or (ii) good correlation between dissociation and a lethal phenotype are selected. Such target cells with low background dissociation rates provide good levels of enrichment for, e.g., apoptotic cells, and the enrichment may be further enhanced by collecting more than one population of dissociated cells. The background rates of dissociation are evaluated for a given target cell type. In many instances, a rate of up to 1% or 1% or 2% is most preferred, with background rates of 2–5%, and upward to about 10% still providing adequate differentiation for use in the invention. Such selection and optimization of a target cell line and its characteristics are well within the skill of the art.

As described more fully elsewhere herein, colon cancer cell lines such as, e.g., HT29 and SW620, breast cancer cell lines such as, e.g., T47D, and HUVEC cell lines are particularly preferred for floater assay embodiments. In still other embodiments, the negative selection strategy may be applied to other cell types, with minor modifications that are within the skill of the art. Non-limiting examples include a wide variety of virally-infected mammalian cells in which cytotoxic agents are selected on the basis of selective killing of virally-infected cells.

Genetic Libraries

The present invention may screen a variety of types of genetic material for cytotoxic agents. For ease of handling and introduction into a cell, such genetic material is frequently in the form of a genetic library, which in turn is incorporated into an expression vector that is suitable for the target cell of choice.

In some instances, the genetic library may be DNA encoding a wholly or partially randomized peptide library, which is synthesized using techniques familiar to those of skill in the art. In other embodiments, the genetic library may encode specific peptide sequences. Such peptide-encoding DNA may be expressed as part of a scaffold structure, with the insertion sites being internally located or, alternatively, located at or near the N-or C- terminus of a scaffold polypeptide. The art is familiar with a wide variety of such scaffolding structures. One non-limiting example of such a randomized peptide library inserted into internal scaffold sites is Abedi et al, N.A.R. 26(2):623–630 (1998), the disclosure of which is incorporated by reference in its entirety.

In other instances, the genetic material to be screened for cytotoxic agents is derived from cellular sources. Such genetic libraries may either be derived from genomic DNA (gDNA), cloned DNA, or from cDNA derived from cellular RNA. Such libraries may be derived from a wide variety of cellular sources, including without limitation brain, human placental tissue, liver, kidney and the like. Preferably, one generates a sufficient number of fragments of DNA so as to ensure that all protein domains are likely to be expressed in the library. E.g., Sambrook, *Molecular Cloning: A Laboratory Manual*, 2nd ed., Cold Spring Harbor Laboratory Press (1989), Chapters 7–9, the disclosure of which is incorporated by reference. The art is well versed in preparing a wide variety of such cDNA and gDNA libraries.

As one non-limiting example, synthesis of cDNA and cloning are accomplished by preparing double-stranded DNA from random primed mRNA isolated from, e.g., human placental tissue. Alternatively, randomly sheared genomic DNA fragments may be utilized. In either case, the fragments are treated with enzymes to repair the ends and are ligated into a vector suitable for introduction into the target cell of interest, which in many cases will be a mammalian cell. Exemplary vectors include a variety of retroviral constructs, some nonlimiting examples of which are described herein.

Cytotoxic Agents

A variety of cytotoxic agents are within the scope of this invention. For example, the cytotoxic agent may be a proteinaceous compound (e.g., a peptide, polypeptide or protein of natural or synthetic origin), a nucleic acid agent (e.g., an RNA acting in an antisense manner or otherwise interfering with normal cellular functions), or a small organic molecule (e.g., a natural product or member of a combinatorial chemistry library, or derivatives thereof).

When the cytotoxic agent is proteinaceous or is a nucleic acid, then the DNA encoding such agent is readily introduced into the cell via standard techniques of molecular biology appropriate for such target cells—e.g., retroviral transfer, electroporation, and the like. When the cytotoxic agent is a small organic molecule, then the target cells are exposed to such agents via a culture medium into which a preselected concentration of the agent has been added.

Cytotoxic agents that are small organic molecules may be readily identified in at least two methods that are familiar to those of skill in the art. One such method is a standard in vitro displacement assay. In such assays, a cytotoxic polypeptide and its corresponding endogenous cellular binding partner are first prepared in vitro, often in a multi-well plate suitable for high-throughput mechanized assay systems. Next, a library of small organic molecules screened to identify those molecules that bind to one of these cellular components, thereby disrupting the normal, endogenous interaction between them. Alternatively, the small organic molecules are obtained by systematically altering the structure of the molecule and correlating that structure to a resulting biological activity—termed here, a "structure-activity relationship" study. As one of skill in the art appreciates, there exist a variety of standard methods for creating such a structure-activity relationship. In some instances, the work may be purely empirical, and in others, the three-dimensional structure of the endogenous polypeptide may be used as a starting point for the rational design of a small molecule mimetic.

Exposure of Target Cells to Cytotoxic Agents

The cytotoxic agents may be proteinaceous (proteins, protein fragments or domains, polypeptides or peptides) or nucleic acid moieties that interact with endogenous components of a target cell, or other organic or bioinorganic compounds. Proteinaceous and nucleic acid agents may be presented to the target cells as products of expression libraries comprised of, e.g., synthetic DNA, cDNA or fragmented, sheared or digested genomic DNA ("genetic libraries"). The genetic library inserts may be expressed in cells without any additional sequences joined to them, or alternatively may be fused to other molecules. For example, a polypeptide may be fused to the perturbagen to increase stability of the perturbagen in the assay system and/or to provide an easily detectable feature, such as fluorescence. Examples of such fusion moieties include GFP, LacZ or Gal4. Details are provided in co-pending, co-owned U.S. Ser. No. 08/965,477, "Methods And Compositions For Peptide Libraries Displayed On Light-Emitting Scaffolds," the disclosure of which is incorporated herein in its entirety.

In some embodiments, genetic libraries encoding or comprising putative cytotoxic agents are presented to the target cell via a retroviral vector, using transfection procedures familiar to those of ordinary skill in the art. Alternatively, such material may be presented to the cell via electroporation or other standard techniques.

Floater Cell Assays and Enrichment

In some embodiments of the invention, the lethal phenotype (e.g., apoptosis or necrosis) is selected for by using a negative selection assay that uses as a surrogate the selection property of disattachment from a culturing surface—referred to herein as a "floater assay." Accordingly, a cell population that is enriched or even highly enriched in cells displaying the lethal phenotype may be collected simply by collecting the cells that "float" in the culture media after exposure to a cytotoxic agent.

Such a floater assay embodiment first involves the selection of a suitable target cell type, for example a cell type that correlates to a tissue or disease state of interest and which displays a suitably low background of spontaneous disattachment (i.e., disattachment of non-apoptotic cells), and high correlation between disattachment and a lethal phenotype following exposure to a lethality-inducing dose of a cytotoxic agent. Suitable cell types can be selected as follows. First, a cell type relating to the disease of interest (described in more detail above) is selected. Next, a cell culture is established using standard techniques. Then the cell culture is separated into two populations—"floaters" and adherent cells. The "floater" population is recovered by withdrawing the culture medium from the culture plate or flask, and then culling the cells from that medium. The adherent population is obtained by trypsinizing the cells that remained adhered to the culture support following withdrawal of the culture medium. Each population is then counted, and the relative number of spontaneous floaters to adherent cells is calculated. The floater cell and adherent cell populations are then analyzed to determine the number of apoptotic or necrotic cells in each. Preferred cell types provide a high correlation between the lack of adherence and the lethal phenotype—i.e., the floater population is relatively heavily populated with dead or dying cells, while the adherent population is relatively heavily populated with viable cells.

Floater cells may present differing concentrations of lethal and non-lethal phenotypes, depending on the cell type from which they are derived. For example, in some cell lines, viable cells (i.e., healthy, living cells that are still undergoing cellular division and/or which are not replicating but which still display normal cellular metabolism and physiology) are not adherent. In such cell lines, the surrogate phenotype of non-adhesion does not correlate to apoptosis, and thus such cell lines are not suitable for the floater assay technique described herein (but may be used for negative selections using direct recovery of genetic material from dead or dying cells culled by, e.g., FACS analysis). In other cell lines in which viable cells normally adhere to a plating surface, a significant percentage of the viable, non-apoptotic cells may enter the floater cell populace. In other cell lines, some significant proportion of the floater cell populace may be non-apoptotic, non-viable cells—for example, cells that have died from cellular processes other than apoptosis. Cell lines providing such mixed "floater" populations can be utilized the assay techniques described herein if suitable controls are employed and/or a second, independent identification method (e.g., Apo 2.7 or Propidium Iodide) is utilized in conjunction with the floater assay technique.

Next, the chosen cell type is then exposed to the putative cytotoxic agents. If the cytotoxic agent is or is encoded by nucleic acid, then this is readily accomplished by providing a population of the selected cell type with a library encoding a variety of such agents, for example by following standard procedures for the construction and infection of retroviral libraries. The treated target cells are then cultured for sufficient time to ensure establishment of the lethal phenotype, following which the "floaters" or disattached cells in the cell culture medium are collected and processed to extract the genetic material. The DNA from the dead or dying cells is then amplified, and at least partially sequenced in order to identify what cytotoxic agent(s) correlate to the apoptotic lethal phenotype. The correlation between the lethal phenotype and the recovered agent may then be checked by introducing such agent into a second such population of target cells, and verifying the presence of the correlative lethal phenotype.

Alternatively, the floater cell population as a whole can be utilized as a subpopulation that has been enriched for one or more lethal phenotypes. When one wishes to distinguish, e.g., apoptotic cells from necrotic cells, then the above strategy may be used to enrich a given target cell subpopulation for lethal phenotypes. The enriched subpopulation may then be further segregated using, e.g., an apoptosis-specific identification strategy (e.g., Apo 2.7) and FACS sorting to obtain a purified apoptotic cell fraction.

Recovery of Genetic Material

Once the cells bearing the putative cytotoxic agents have been screened and those cells having a lethal phenotype either identified, directly via a staining technique or indirectly via a surrogate phenotype such as lack of adhesion, the genetic material from those cells is recovered via standard techniques. Briefly, standard PCR techniques are used to rescue and amplify the genetic material (DNA) of interest. PCR primers are selected so as to amplify the region encoding the putative cytotoxic agents. The genetic material may then be wholly or partially sequenced using techniques familiar to those of skill in the art, and can be re-constituted as a sublibrary for a second selection or for a counterselection.

Endogenous Cellular Proteins

After completion of the negative selection protocols as described herein, it is often advantageous to obtain the endogenous cellular protein(s) that promote the lethal phenotype. By "endogenous cellular protein" is meant a protein, polypeptide or aggregate of polypeptide subunits that are encoded by the native genetic material resident in the selected host cell. Such endogenous cellular proteins may serve a variety of functions in the cell, including without limitation (i) enzymatic function, (ii) protein-protein interaction in a pathway in the cell cytoplasm or nucleus; and (iii) transmembrane or secreted proteins, including signalling and transport proteins and the like.

Endogenous cellular proteins of interest can be obtained by a variety of methods. For example, if the cytotoxic agent is proteinaceous, then the corresponding endogenous binding partner may be identified via standard protein-protein interaction methodologies such as the yeast two-hybrid binding assay, phage display techniques or in vitro binding assays utilizing, e.g., protein-encoated substrates.

Assaying for Cell-specific Cytotoxic Agents

In some embodiments, the inventive methodology may be applied to identify agents that exert a differential cytotoxic effect—i.e., are cytotoxic to one cell population but not to another. Such embodiments are particularly advantageous for identifying agents that will act with specificity against a given cancer type, while leaving non-cancerous cells partially or wholly unaffected. Similarly, the methodology can identify agents that are specific to cancer cells in one developmental stage but not another—e.g., metastatic cells. Such applications are particularly advantageous in that the agents so identified are expected to provide therapeutic advantages such as lack of undesirable side effects, lower therapeutic dosages, and the like.

One general approach is as follows. The negative selection strategy for selecting lethal phenotypes (e.g., apoptosis) is implemented as described above, utilizing the cell type against which a cell-specific agent is sought. Upon completion of this step, the genetic material encoding or embodying the cytotoxic agents is isolated, and reintroduced into a second population of cells that is or is representative of the cell type for which it is desired that the cytotoxic agent be relatively or completely non-toxic. In this second counterselection step, one of two strategies may be employed. First, the cells exhibiting a lethal phenotype may be collected and the corresponding genetic material be evaluated so as to eliminate putative cell-selective agents (as having been demonstrated to be non-cell specific). Conversely, the counterselection step may employ a positive selection strategy—i.e., isolating the genetic material that corresponds to the cells in the second population that do not exhibit the lethal phenotype—i.e., continue to grow in the presence of the cytotoxic agent.

Assaying for Conditional Cytotoxicity

The basic negative selection strategy described above may be modified slightly to identify agents that increase sensitivity of a target cell to a known cytotoxic agent (termed herein, "conditional cytotoxicity"). Such embodiments are particularly advantageous for identifying agents that can be used as an adjuvant, given in conjunction with the known cytotoxic agent. Such a strategy permits a lower dosage of the known cytotoxic agent to be administered, with correspondingly lower incidence or severity of unwanted side effects.

One general approach is as follows. A target cell type is selected, and a cytotoxic substance of interest (referred to herein as a "secondary reagent") is selected. Next, a "standard kill curve" (i.e., dose-response curve, wherein increasing amounts of agent are presented to target cells, and the resultant cell death monitored and plotted) is prepared for that cell type and cytotoxic substance. From the standard kill curve, a "subtoxic threshold" dosage of the secondary reagent (i.e., the largest dosage from the kill curve that does not initiate cell death in the target cell population) is selected for further study. A population of the target cells is then provided with one or more putative cytotoxicity-enhancing agents (e.g., in the form of a genetic library), and subsequently exposed to the selected subtoxic threshold dosage of the secondary reagent. A negative selection as described elsewhere herein is then conducted, and transformed target cells that die in response to the subtoxic amount of the secondary reagent are collected and the corresponding cytotoxicity-enhancing agent identified. If that agent was a proteinaceous or nucleic acid biomolecule, then the genetic material that encodes or comprises the agent is isolated and evaluated, for example by the PCR amplification and sequencing strategy described elsewhere herein. Preconditioning In some embodiments of the invention, a preconditioning step may be added to the negative selection strategy. In such embodiments, a population of target cells is first exposed to a preconditioning agent. The cells are then exposed to the putative cytotoxic agents (e.g., a genetic library). Again, the selection collects cells displaying a lethal phenotype (e.g., apoptosis or necrosis), and isolates the corresponding cytotoxic agents, as described elsewhere herein. This step results in the identification of agents that act in the presence of the preconditioning agent.

Optionally, a second selection step (a positive selection) may be used to identify agents that act only in the presence of the preconditioning agent. In such an embodiment, a second population of the target cell is exposed in a similar manner to the cytotoxic agent(s) isolated in the first (negative) selection step, but without the prior step of exposure to the preconditioning agent. Cells that live are collected, and the corresponding cytotoxic agent identified, as described elsewhere herein.

A variety of preconditioning agents will be known to those of skill in the art. Generally, these agents will be involved in metabolic pathways related to cellular growth or death. Non-limiting examples include growth factors such as the activated EGF receptor, activated oncogenes such as ras or myc, knockouts of genes such as p53, p16 or Rb, and the like.

The following examples for the generation and use of the selection systems of the invention are given to enable those skilled in the art to more clearly understand and to practice the present invention. The present invention, however, is not limited in scope by the exemplified embodiments, which are intended as illustrations of single aspects of the invention only, and methods and materials that are functionally equivalent are within the scope of the invention. Various modifications of the invention in addition to those described herein will become apparent to those skilled in the art from the foregoing description and accompanying drawings. Such modifications are intended to fall within the scope of the appended claims.

EXAMPLES

Example One

Methods for Identifying and Characterizing Dead and Dying Cells

Many negative selections, including some selections described herein, require the identification of dead and/or dying cells. As one of ordinary skill in the art appreciates, there are many techniques that can be used to detect these cells.

A number of techniques exist for identifying cells that have a lethal phenotype, and for distinguishing, e.g., apoptotic and necrotric cells. In some instances, antibodies are used to identify cells that are undergoing apoptosis. Koester et al., Monitoring Early Cellular Responses in Apoptosis is Aided by the Mitochondrial Membrane Protein-Specific Monoclonal Antibody AP02.7" Cytometry, 29:306–312 (1997). In some such embodiments, the antibodies recognize antigens that are, under normal (viable) conditions, hidden or masked from detection, but which become exposed in dying cells. In other instances, apoptotic cells are detected using substrates that are recognized by proteases (caspases) that are unique to, and activated by, the apoptotic pathway. Green, D., Kroemer, G.,"The Central Executioners of Apoptosis: Caspases or Mitochondria". Trends in Cell Biology. 8:267–271 (1998). In still other instances, dead and dying cells are distinguished from viable cells on the basis of their interaction with various dyes. One class, membrane permeable dyes (e.g. Trypan Blue), are actively excluded from the intracellular compartments of living cells but accumulate in the cytoplasmic/nuclear regions of dead or dying cells. A second class of reagents, membrane impermeable dyes, is excluded from all living cells, but is capable of penetrating the compromised membrane boundaries of dead and/or dying cells. Many of these reagents (e.g. propidium iodide, ethidium homodimer) have an affinity for DNA and show an increase in fluorescence upon binding to nucleic acids. Krishan, "Rapid flow cytofluormetric analysis of mammalian cell cycle by propidium iodide staining," J. Cell Biology 59:766 (1973). These reagents may be used in conjunction with FACS analysis or be applied in the more general techniques of fluorescent microscopy. Shapiro, "Practical Flow Cytometry", H. M. Wiley-Liss Publications (1995).

A. Apo 2.7 Antibody Staining.

Apo2.7 (Coulter Immunotech) is a monoclonal antibody that recognizes an epitope in the mitochondrial membrane that is exposed only in cells that are undergoing apoptosis. To test its efficacy in negative selections, $1 \times 10^6$ Jurkat cells in 2 milliliters of AIM-V serum free medium were induced to undergo apoptosis using the anti-FAS antibody (lug/ml anti CD95 clone, Yonehara, S. et al., "A cell killing monoclonal antibody (anti-FAS) to a cell surface antigen co-down regulated with the receptor of tumor necrosis factor." J. Exp. Med 169: 1747–1756 (1989)). After a fixed period of exposure (0, 2, 10, 17, or 21 hours in anti-FAS antibody), 100 $\mu$l of a 100 $\mu$g/ml solution of digitonin in PBS was added (20 minutes on ice) to permeablize the cell membrane. Following this procedure, the cells were spun (200×g) and resuspended in a solution containing a fluorescent R-phycoerythrin-cyanin labeled Apo2.7 antibody provided by Coulter-Immunotech (10 $\mu$l Apo2.7 antibody, 90 $\mu$l PBS,+cells). This reaction was allowed to incubate for 15 minutes at room temperature in the dark. The cells were then pelleted by centrifugation (200×g) and resuspended in 1 ml of PBS before being analyzed by flow cytometry (excitation, 488 nm; emission, 660–690 nm). Results of FACS analysis (FIG. 1) showed that at time=0 (i.e. control), only 4% of the population labeled with Apo2.7 antibody. In contrast, exposure to the apoptotic-inducing anti-FAS antibody led to increased binding of Apo2.7 to the Jurkat cell line (t=21 hrs=81% labeling).

B. Propidium Iodide Staining.

Propidium iodide (PI) is a fluorescent, DNA intercalating, molecule. Live cells with intact membranes exclude PI from intracellular compartments and thus are non-fluorescent. Dead and dying cells whose membranes have been compromised are permeable to PI, and thus are fluorescent. The PI staining technique is equally applicable to apoptotic and necrotic cells.

As a non-limiting example of the use of this type of reagent for identification and purification of dead cells, the following pilot experiment was performed. Floater cells (i.e., non-adherent cells in an otherwise adherent cell population) were isolated from a flask of HT-29 colon cancer cells. These cells, along with an equally sized adherent cell population, were harvested by centrifugation and subsequently resuspended at $1 \times 10^6$ cells/ml in PBS. PI was then added to each sample at a concentration of 2.0 $\mu$g/ml and cells were analyzed by flow cytometry (excitation 488 mn, emission, 610 nm). Dead cells that had lost membrane integrity could be easily distinguished from live cells based on their increased fluorescence (FIG. 2). The percentage of adherent cells that were positive for PI uptake averaged approximately 0.5–1.5% at this cell density. In non-adherent "floater" cells, a higher percentage of cells (>10%) were observed to be positive for PI uptake.

To make a positive correlation between PI staining and cell viability, an equivalent number of PI positive and PI negative cells were identified and collected separately using FACS. These two populations were then plated onto 150 mm plastic tissue culture dishes and allowed to attach and grow for 7–10 days. Cell viability was then determined by counting the number of colonies that grew on each plate. While cells that were PI negative were viable and produced colonies, PI positive cells failed to grow.

C. Nuclear Condensation.

In contrast to necrosis, cells that die by apoptosis often exhibit nuclear condensation. Thus, dye/stain techniques that allow visualization of the nuclear morphology are used to assess the method by which a cell dies.

Two cell lines, WM35 and HS294T, were plated out (50,000 cells per well, 24 well plate) and allowed to adhere. After 24 hours, the cells were treated for 4 hours with varying concentrations (5–80 $\mu$M) of Cisplatin (cis-platinum (II) diammine dichloride), a well-known chemotherapeutic agent that induces apoptosis. The following day (18–24 hrs later) the media was then collected from each well and cells that did not adhere to the well (termed herein, "floaters cells" or "floaters") were collected by centrifugation (400×g). Adherent cell populations were then lifted from the solid support by trypsinization, centrifuged (400×g), and resuspended in PBS (0.125 ml). To observe the nuclear morphology and percent cell death in the WM35 and HS294T cell lines, cells from both floater and adherent populations were stained concurrently with Syto16 and ethidium homodimer (125 ul of cell suspension+2.5 ul 62.5 uM Syto16+2.5 uM 100 ug/ml ethidium homodimer, 10 minutes at 37° C.). Ethidium homodimer is a membrane impermeant compound that fluoresces in the 617 nm range when it is intercalated with chromosomal DNA. Thus, in a mixed cell population containing both living and dead/dying cells, only those cells whose membranes have been compromised will stain with ethidium homodimer. In contrast, Syto 16 (Molecular Probes) is a membrane permeant dye that fluoresces in the 518 nm range when associated with chromosomal DNA. Together, these two dyes can be used to observe and distinguish the nuclear morphology in a population containing both living and dead/dying cells.

Examination of the floater population of Cisplatin treated HS294T cells showed that while greater than 50% of the cells stained with ethidium homodimer, in general, fewer than 20% of these cells showed condensed or fragmented nuclei when observed by fluorescent microscopy. Instead, the nuclei in these cells appeared diffuse and bloated, suggesting that Cisplatin treated HS294T cells die by a necrotic, rather than an apoptotic, pathway. In contrast, the floaters obtained from Cisplatin treated WM35 cell lines showed both a high degree of ethidium homodimer staining (45–50%) and a phenotypically distinct condensed or fragmented nuclei (40–50% in higher concentrations of Cisplatin) suggesting that a large percentage of these cells die by an apoptotic pathway. Neither of the two adherent cell populations exhibited significant amounts of ethidium homodimer staining (generally <10%), indicating that the adherent population largely comprised viable cells.

D. Caspase-Sensitive Dyes.

Caspase-3 and other proteases have been shown to play a role in apoptotic induced cell death (Green and Kroemer, 1998). To test the correlation between this enzymes activity and cell death, and to study the possibility of using caspase-3 activity in negative selections, WM35 (melanoma) cells are induced to undergo apoptosis and then exposed to Rhodamine 123-YVAD, a caspase-3 fluorescent substrate.

WM35 cells were passed one day prior to induction of apoptosis and incubated for 24 hrs to allow the cells to attach to the substrate. The media was subsequently removed, the remaining adherent cells washed 1× with PBS, and subsequently exposed to Cisplatin (15 $\mu$g/ml) in fresh media. Eighteen to twenty-four hours after the induction of apoptosis, the floater cell population was collected, pelleted by centrifugation (400×g), and resuspended at 3×10$^6$ cells/ml in PBS. Samples were then split into four groups: (1) uninduced minus Rhodamine 123-YVAD (substrate), (2) uninduced plus substrate, (3) induced minus substrate, and (4) induced plus substrate. For samples exposed to Rhodamine 123-YVAD substrate, 50 ul of a pre-warmed (37° C.) cell suspension was combined with 25 ul of a stock substrate solution (Cellprobe). Samples were incubated for 60 minutes at 37° C. and then placed on ice prior to FACS analysis. In addition to caspase-3 staining, a replicate of each sample was stained with propidium iodide to determine the percentage of cells within the population whose membranes had been compromised and the overlap between PI and caspase-3 staining. For flow cytometric analysis, each sample was brought to a total volume of 1 ml (PBS) and excited at a wavelength of 488 nm (15 m watts) using an argon laser. Emission spectra were read at 515–535 nm wavelength using the FL1 (PMT2) 525 nm blue filter.

Caspase-3 activity peaks early in the apoptotic cycle, long before the disruption of the cell cytoplasmic membrane. Therefore, caspase3-positive floater cells are predicted to be PI-negative, while PI-positive floater cells are expected to have passed the peak period of caspase-3 activity and therefore be phenotypically caspase-3-negative. Consistent with these predictions, of the PI-minus, Cisplatin-treated WM35 cells collected from the floater population, 94.6% were found to be caspase-3 positive. The remaining cells obtained from the floaters fell into the PI-positive, caspase-3-negative group. Control studies with adherent cell populations showed the vast majority (>95%) to be both caspase and PI negative.

Example Two Identifying Cell Types for Negative Selections via Floater Assays

Prior to performing negative selection assays, a cell line with a phenotypic feature that is a readily monitored surrogate for a lethal phenotype is identified. In this Example, lack of cellular adhesion to a plastic, gelatin or other suitable culturing support (i.e. presence of "floating cells" or "floaters") is selected as the surrogate phenotypic feature that correlates to the lethal phenotype.

In order to use floater populations as a method of identifying and enriching for dead and/or dying cells in a negative selections, cell lines preferably display three features: (1) in a stable untreated cell population, the greater majority of cells are adherent to the solid support (e.g. plastic, gelatin) and the background rate of floater cells is relatively low (<1%); (2) in an untreated or treated cell population (i.e. one exposed to putative cytotoxic agents and optionally also a secondary agent), a high percentage of the floater cells correlate with the dead and/or dying cell population; and (3) the cell line is receptive to standard or common techniques of introducing library inserts encoding putative cytotoxic agents into the cell e.g. retroviral infection or transduction.

A. Background Levels of Floater Cells.

The first variable, background floater levels, are evaluated by establishing a stable culture of target cells and then comparing the levels of cells floating in the media with the total number of cells (adherent cells+floater cells). Additional procedures, such as retroviral infection, can be overlaid on top of this experimental design, thus making it possible to assess the effects of retroviral infection on floater cell/ total cell ratios and determination of the receptiveness of the cell line to the introduction of putative cytotoxic agents by transfection.

HT29 cells were tested for feasibility in the floater cell assay as follows. Briefly, six flasks were inoculated with $6.25 \times 10^5$ HT29 cells/flask on Day 0. On Day 1, after the cells had been allowed to adhere to the solid support, two of these flasks were infected with retroviral supernatant containing the retroviral vector pVT324, which includes a selectable drug resistant marker (e.g. neomycin), and which constitutively expresses a green fluorescent protein. Of the remaining four flasks, two were mock infected (i.e. exposed to all of the same reagents/conditions as flasks 1 and 2, minus the retrovirus, see "Example 3C") and two were left undisturbed. On Day 2, this procedure was repeated (i.e. a double infection). On Day 3 (and subsequently on Day 5) one flask was selected from each of the three groups and processed by separating and counting the floater and adherent cell populations. In the case of the floater cell population, the media was collected, centrifuged at 200×g for 10 minutes, and resuspended in PBS prior to removing a sample for counting on a hemocytometer. For the adherent cell population, cells were first removed from the flask by trypsinization, centrifuged, and then processed for analysis in a fashion analogous to the floater cells. To determine the inherent background level of floater cells present in the population, the ratio of the number of floater cells to the total number of cells (adherent cells+floater cells) was analyzed on both the Day 3 and Day 5 flasks that had not been manipulated. These numbers were compared with the analogous numbers taken from infected and mock-infected flasks to determine whether the retrovirus or transfection procedures altered background floater rates. To determine the susceptibility of HT29 cells to retroviral infection, the fraction of cells that expressed GFP in pVT324 infected flasks was calculated using flow cytometry.

Figure 3:
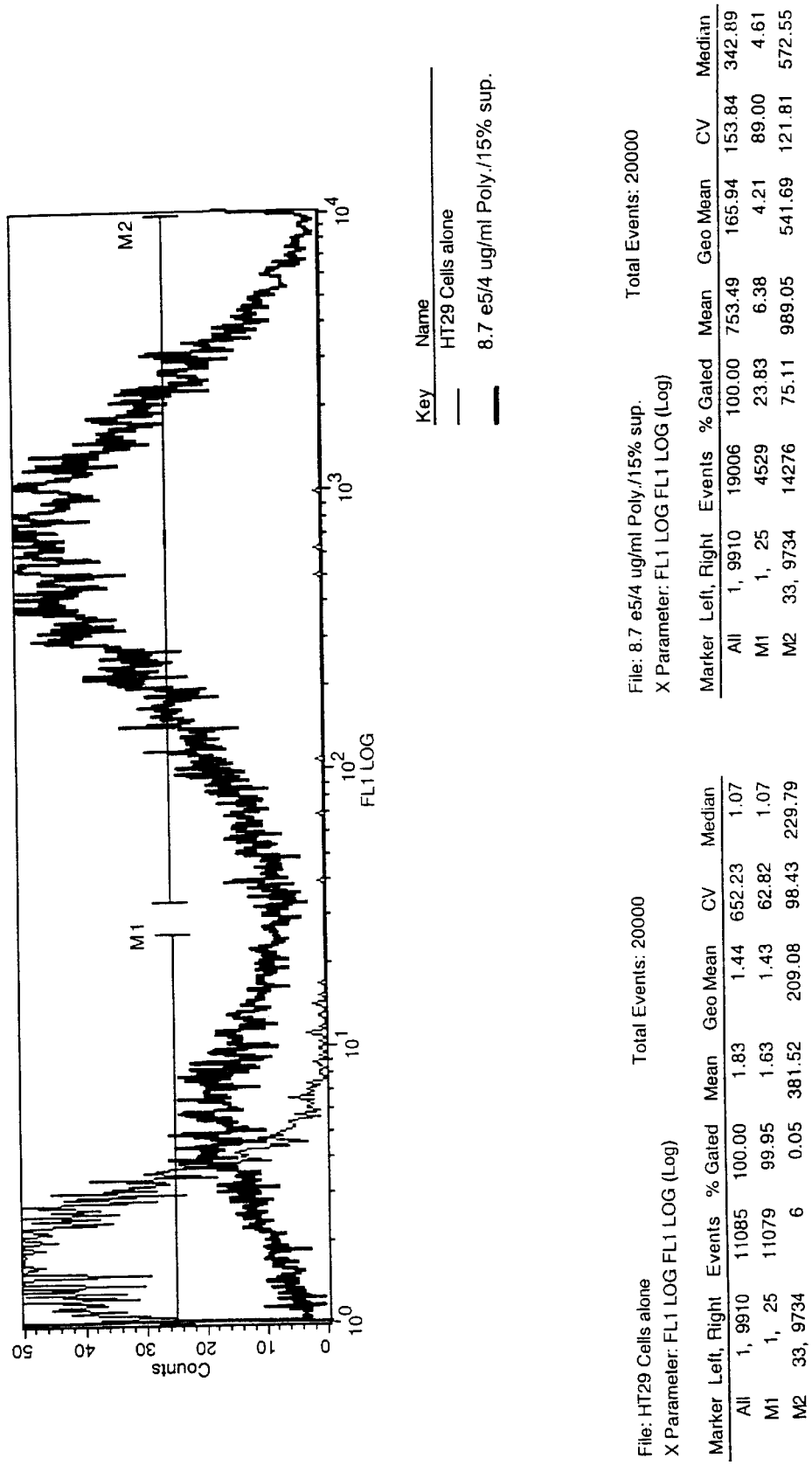
FIG. 3 is the FACS analysis of uninfected and mock-infected HT29 cells. The mock-infected cells contain a GFP marker.

The non-infected background floater rate of the HT29 cell line was found to be 0.42%. Infected and mock infected HT29 cells showed 0.51 and 0.37% floater rates respectively, indicating that neither the retroviral infection procedures nor the retrovirus itself increases background floater rates substantially. In addition, FACS analysis of the pVT324 infected HT29 population showed approximately 80% of the cells falling into the "bright" gate (i.e. GFP expressing cells). FIG. 3. Together, the low background floater rate and the high susceptibility of HT29 to retroviral infection make it a desirable candidate for negative selections. Additional cells lines—two colorectal adenocarcinoma lines, SW620 and DLD-1 (CCL-221, ATCC), and a prostate adenocarcinoma cell line, PC-3—also were examined using these same criteria and been found to be suitable cell line candidates for negative selections. In contrast, LNCaP, a human prostate carcinoma cell line (ATCC), exhibited background floater rates of greater than 10% thus making it less preferred for use in negative selections which utilize lack of adhesion as a surrogate for a lethal phenotype. See Table 1, below.

TABLE 1

|  | Colon HT29 | Colon SW620 | DLD-1 | Prostate PC-3 | Prostate LNCaP |
|---|---|---|---|---|---|
| Background Death | ≦1.0% | ≦1.0% | ≦1.0% | ≦1.0% | 4–5% |
| Floaters | ≦0.5% | 1.0% | 0.5% | 2.5% | ≧10% |
| Fraction of dead cells in floaters | 40% | 65% | 50% | 30% | 12% |
| Do dead cells eventually become floaters? | YES | YES | YES | YES | ? |
| Tolerates retroviral infection | YES | YES | YES | YES | YES |

B. Correlation Between "Floaters" and Lethal Phenotypes.

An important component to the negative selections of the present invention is the ability to demonstrate a correlation between the floater population and dead and/or dying cells. This correlation can be established using a variety of techniques known to those of skill in the art, including without limit those described above for detecting and characterizing such cells.

In this Example, propidium iodide (PI) was used as a method of monitoring the percent dead/dying cells in both the adherent and floating cell populations. To determine the percent of floaters that were dead and/or dying, four separate cell lines (three colon cancer cell lines, HT29, SW620, and DLD-1, and one prostrate cancer cell line, PC3) were plated in tissue culture flasks and allowed to adhere. After 24–48 hours, both adherent cells and floaters were collected, stained with PI, and examined by flow cytometry. While the adherent populations of all four cell lines typically showed less than 1% $PI^+$ cells, 30% or more of the floater cell population were observed to be $PI^+$.

These studies demonstrate that there is a strong correlation between cell death and floaters in the above cell lines. In addition, combining the techniques of floater collection with a second selection (FACS sorting of $PI^+$ cells) enables one to further maximize the level of enrichment of dead and/or dying cells having a lethal phenotype and thus, increasing the likelihood of isolating cytostatic agents that exist at low frequency in the population.

Figure 4:
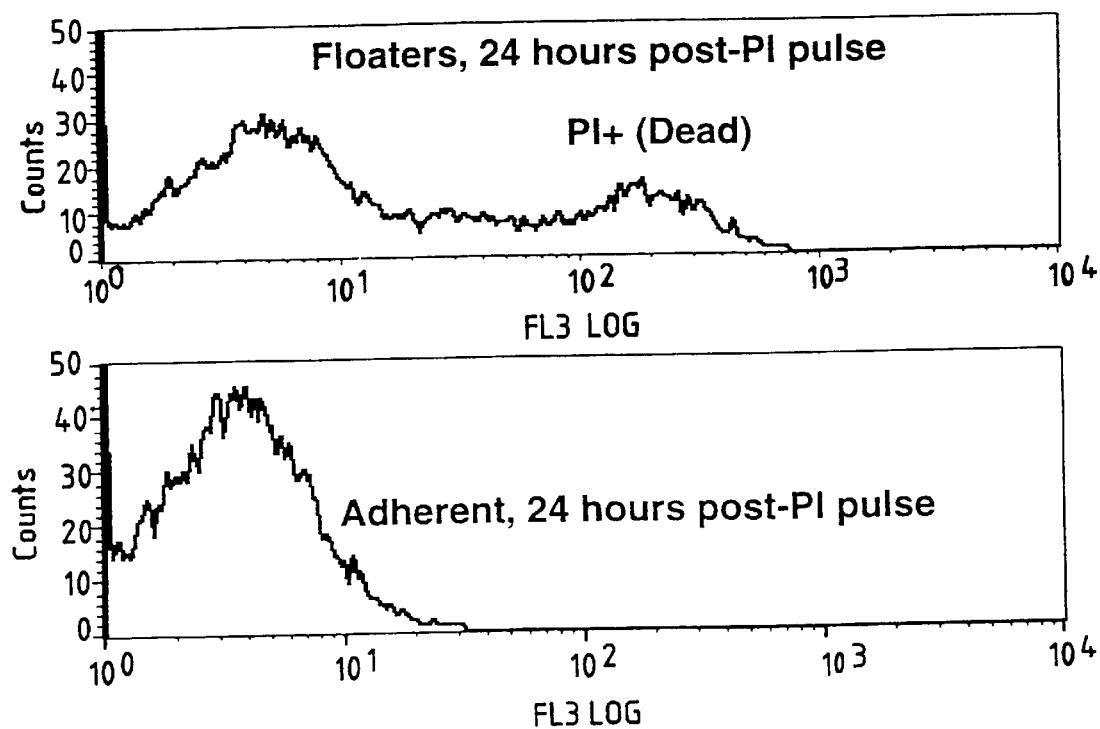
FIG. 4 is the FACS histogram depicting differential patterns of PI staining in floater vs. adherent cell populations, 24 hours after exposure to PI.

A second experiment designed to determine whether dead or dying cells move from the adherent to floater population was performed using a pulse-chase protocol. Alberts, B. et al. "Molecular Biology of the Cell", pg. 180, Garland Publishing, Inc. (1983). Adherent PC-3 cells in culture were stained for a brief period with 2 $\mu$g/ml PI while remaining attached to the plate. The cells were then rinsed and returned to fresh media. Twenty-four hours later, both the floater and adherent populations were collected and scanned to determine the distribution of PI positive cells amongst the two groups of cells. The results (FIG. 4) show that the PI positive cells segregate specifically to the non-adherent "floater" population of cells. This result indicates that dead or dying cells that had previously been adherent move into the floater population within 24 hours.

Example Three

Introduction and Recovery of Sequences Encoding Cyyotoxic Agents

In order to perform "floater assays" to identify sequences that encode cytotoxic agents (i.e., agents that stimulate relatively immediate death of individual cells, or agents that prevent cell growth or proliferation, thus gradually leading to the death of a cell population), libraries of sequences encoding putative cytotoxic/cytostatic agents are constructed and then introduced into the selected cell lines. The following Example describes one non-limiting protocol for such work.

A. Preparation and Transfer of a cDNA Library

Using techniques that are common to individuals familiar with the art, polyA MRNA is isolated from fetal brain tissue by affinity chromatography on an oligo dT cellulose column (polyASpin™, New England BioLabs). This material is then subjected to first strand PCR (Pfu polymerase, Stratagene) synthesis using oligo dT primers linked to sequences encoding a selected restriction enzyme linker. Following the elimination of RNA (RNAse A/H, Boehinger Mannheim) from the sample, second strand synthesis proceeds, using random primed oligos that have been constructed with the desired linker sequence. The double stranded cDNA product is then size selected, treated with the appropriate enzymes to create "sticky" ends, and ligated into an expression vector suitable for the cell line of choice.

As an alternative to oligo dT primed cDNA libraries, randomly primed cDNA libraries are used as a source of sequences encoding putative cytotoxic agents. As one non-limiting example of how to construct such a library, polyA MRNA derived from placental tissue was PCR amplified using a random 9-mer linked to a unique SfiI sequence ("SfiA"), followed by an additional set of nucleotides that is used later for library amplification (OVT 906: 5'ACTCTG-GACTAGGCAGGTTCAGTGGCCA TTATGGCC (N)$_9$) (SEQ ID NO: 1). The product of this reaction was size selected (>400 base pairs) and subjected to RNAseA/H treatment to remove the original RNA template. The remaining single stranded DNA was then subjected to a second round of PCR using a random hexamer nucleotide sequence linked to a second unique SfiI sequence ("SfiB") which was again followed by an additional set of nucleotides for future library amplification: (OVT 908: 5'AAGCAGTGGTGT-CAACGCAGTGAGGCCGAGG CGGCC (N)$_6$) (SEQ ID NO: 2). The final product of this reaction was blunted/filled with Klenow Fragment (New England BioLabs), size selected, PCR amplified (OVT 909: 5'ACTCT GGACTAG-GCAGGTTCAGT (SEQ ID NO: 3) and OVT 910:5'AAG-CAGTGGTGTCAACGCAG TGA) (SEQ ID NO: 4), digested with SfiI (New England BioLabs), and inserted into a retroviral vector.

Alternatively, commercially available libraries can be used. The cDNA inserts of such libraries are spliced out from the original vector and inserted into an expression vector of choice. As one non-limiting example, three libraries obtained from three different tissue sources (brain, liver, and kidney) were obtained from Origene Inc. (Catalogue #DHL101, DHL 105, and DHL 106). Using standard techniques, bacterial hosts carrying the libraries were expanded in liquid media (LB plus ampicillin) and used to prepare large quantities of episomal (library) DNA (Maxiprep, Qiagen). The cDNA insert in each vector was then released by digestion with the appropriate restriction enzyme (EcoRI/XhoI) and the fragments were then gel purified (0.4–2.8 kB) and ligated (T4 Ligase, Boehringer Mannheim) into the compatible sites of the pVT340 retroviral vector (described below).

B. Construction Of A Scaffolded Peptide Library

Figure 5:
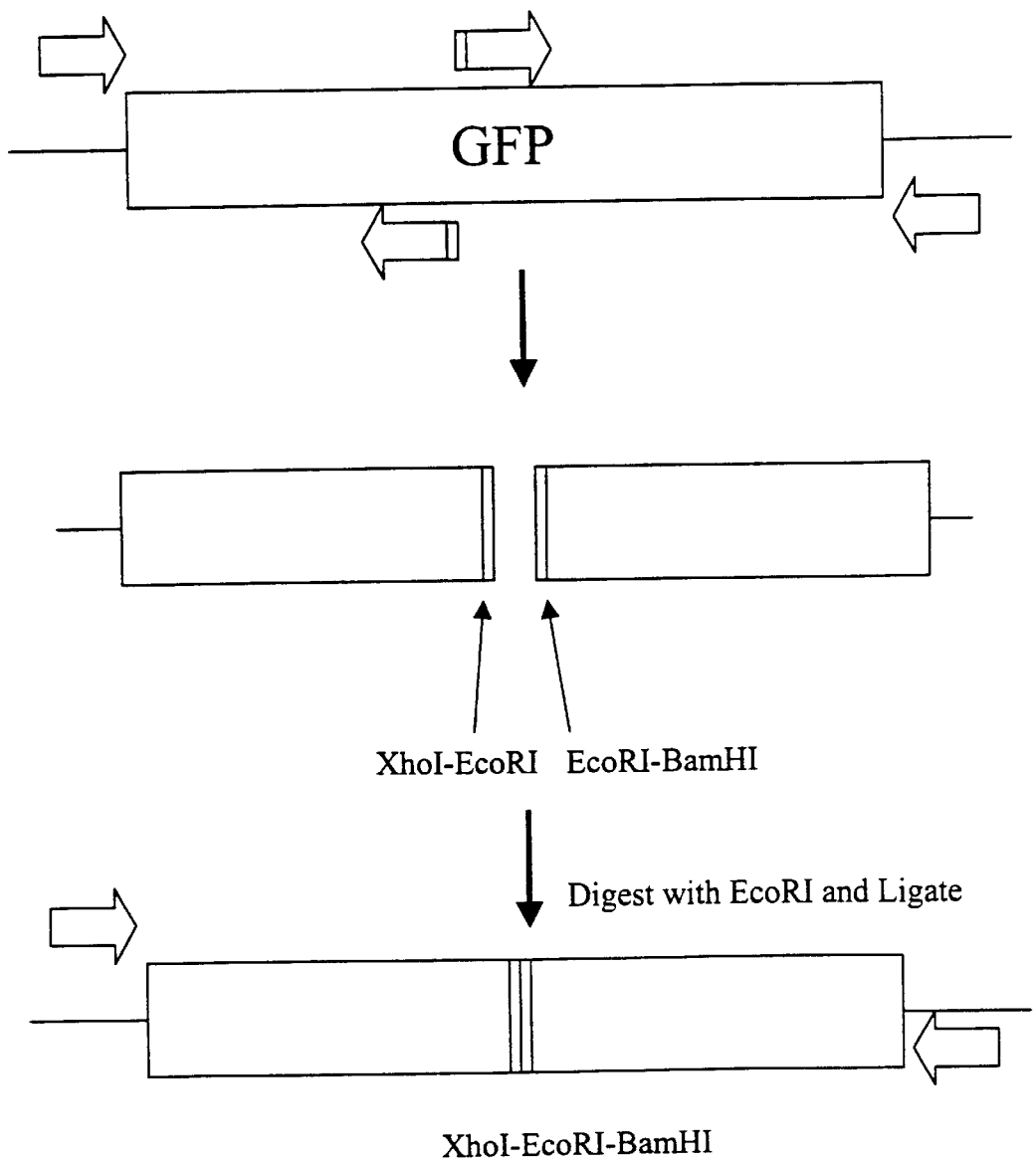
FIG. 5 is a diagrammatic representation of the construction of a GFP reporter vector having internal XhoI/EcoRI/BamHI restriction sites. Two sets of primers were used to PCR amplify the left- and right-hand segments of GFP. The internal primer of each primer set contains either XhoI-EcoRI or EcoRI-BamHI restriction sites, as indicated. The subsequent digest (EcoRI) and ligation of these fragments recreates GFP with a new internal cloning site, XhoI-EcoRI-BamHI. Subsequent PCR amplification with the two external primers allows amplification of the new GFP.

Construction of a scaffolded peptide library followed the protocols developed by Abedi et al., N.A.R. 26(2): 623–630 (1998), incorporated by reference herein in its entirety. Initially a modified GFP containing BamHI, XhoI, and EcoRi sites at position 6 (pVT27) was constructed using pVT014 (also known as pACA151, a gift of Dr. Jasper Rine) as a template. To accomplish this, two separate PCR reactions using oligos OVT 312 (5'TGAGAA TTCCTCGAGTTGTTTGTCTGCCATGATGTATAC) (SEQ ID NO: 5), OVT 322 (5'TGAGAATTCG GATCCAAGAATGGAATCAAAGTTAACTTC), OVT 329 (5'GTTAGCTCACTCA TTAGGCACCC) (SEQ ID NO: 7) and OVT 330 (5'CGGTATAGATCTGTATAGTTCATCC ATGCCATGTG) (SEQ ID NO: 8) were performed using recombinant Pfu polymerase (Stratagene). The internal termini of the resulting fragments contained XhoI/EcoRI and EcoRI/BamHI restriction sites (FIG. 5). The two fragments were subsequently digested with EcoRI (New England Biolabs), ligated with T4 DNA Ligase (Boehringer Mannheim) and PCR amplified using the external primers OVT 329 and OVT330. The final product contains a 6 codon insert incorporating XhoI/EcoRI/BamHI restriction sites at the Gln157-Lys 158 insertion site of pVT27.

To construct the random peptide library, fifteen picomoles of Aptamer 3 (5'TCGAGA GTGCAGGT[NN(G/C/T)]$_{15}$GGAGCTTCTG) (SEQ ID NO: 9) was mixed with Aptamer 4 (5'ACCTGC ACTC) (SEQ ID NO: 10) and Aptamer 5 (5'GATCCAGAAGCTCC) (SEQ ID NO: 11) in a molar ratio of 1:50:50 and annealed in 20 mM Tris-HCl, pH 7.5, 2 mM MgCl$_2$, 50 mM NaCl by heating to 70° C. for 5 minutes. The solution was then allowed to cool to room temperature and ligated to a BamHI/XhoI cut pVT 334 retroviral vector using T4 ligase (Boehringer Mannheim). As a result of these manipulations, a biased-random fifteen amino acid sequence flanked by three constant amino acids on either end was inserted into position 6/VT27 of GFP. The library was transformed into E. coli (DH10B, Gibco) by electroporation and plated on LB-agar plates containing the selective drug, ampicillin.

C. Expression Vectors

A variety of retroviral or other vectors are suitable for use in the invention. As one non-limiting example, of a retroviral expression vector useful for constitutive expression of library sequences in mammalian cells was constructed as follows. The 3.8 kB HindIII/ScaI band of pVT314 (FIG. 18) was ligated to the 1.9 kB SSPI/PvuII band of pBluescript™ (Stratagene). The final product of this reaction (referred to as pCLMFG, or MFG or pVT340) is a vector that contains all the necessary components of a constitutive retroviral expression vector including a Psi site for packaging, constitutive CMV driven expression, a splice donor and acceptor site for obtaining high levels of library insert expression, and a multiple cloning site (MSC) linked to the 3' end of EGFP. Putative cytotoxic agents are expressed constitutively as fusions with the GFP scaffold.

Figure 6:
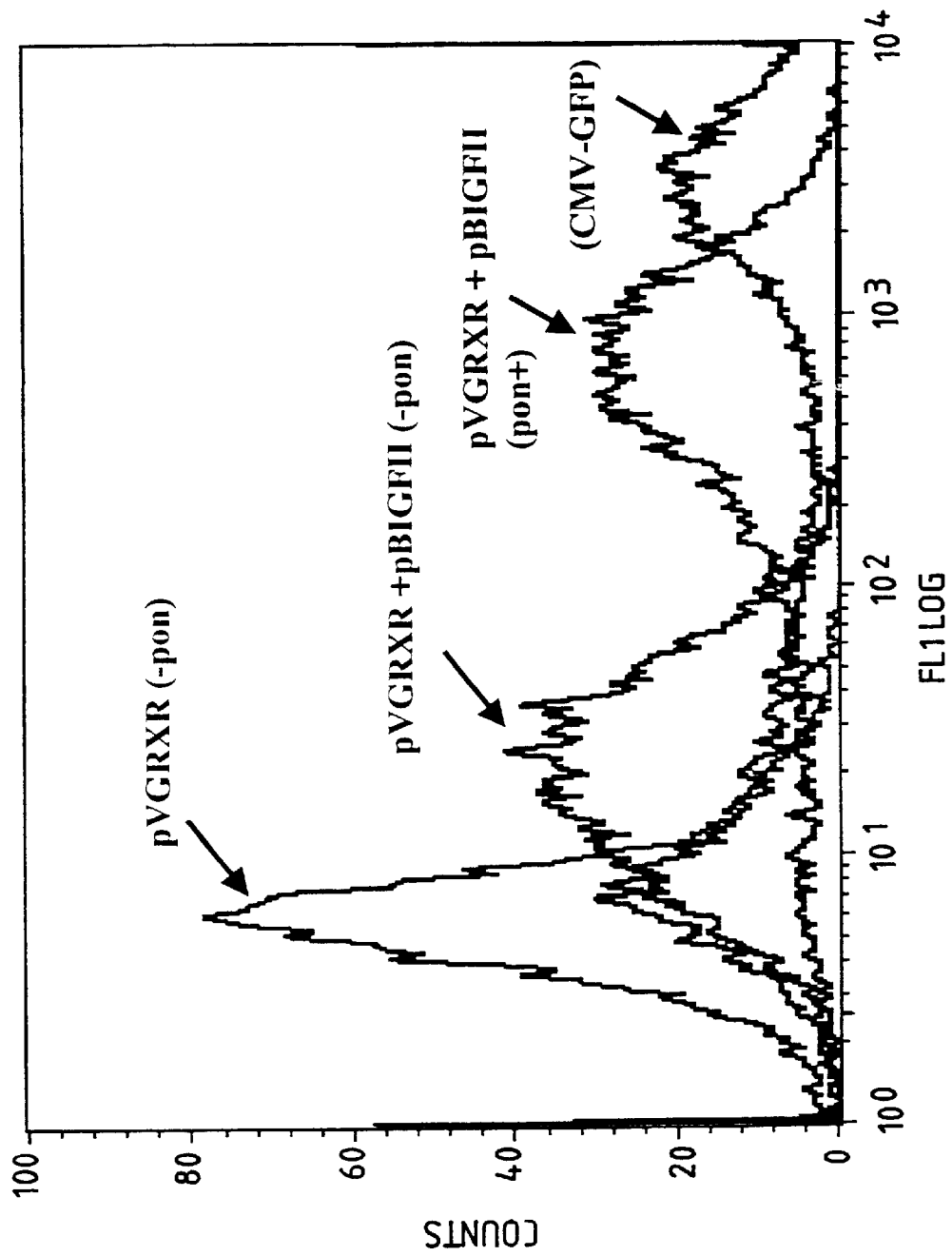
FIG. 6 is a FACS histogram depicting the background fluorescence and induction characteristics of vector pBIG-FII. Also shown are the fluorescence signatures of the vector pVGRXR, and CMV-GFP.

As an alternative to the constitutive pCLMFG vector, an inducible construct that can be regulated by ecdysone was constructed as follows. The PmII/XhoI fragment from pVT324 was inserted into the MCS of the PIND vector (Invitrogen). This product was then digested with BglII, blunt-ended and inserted into a pBabe-K-ras vector (pVT313-based) that had been digested with BamHI/XhoI and blunted (Klenow Fragment). The resulting vector was designated pBabe-Forward-1. The XbaI fragment of pVT324 was then inserted into the compatible site of pBabe-Forward-1. The resulting vector was designated pBIGFII. Vector pBIGFII was subsequently transfected into cells (ECR293, Invitrogen) that contain an endogenous copy of the ecdysone receptor (pVgRXR). When these cells are grown in the absence of ponesterone A, they exhibit a low level of background fluorescence. In contrast, when the cells containing both vectors are grown in the presence of 5 $\mu$M ponesterone A, the level of fluorescence increases by approximately thirty fold (see FIG. 6). Thus, pBIGFII exhibits a low background fluorescence and is strongly induced in the presence of ponesterone A. Such vectors are useful in identifying sequences encoding cytotoxic agents that disrupt the cell cycle or induce death via an apoptotic pathway.

D. Retroviral Packaging and Infection

Next, the library constructs are packaged for retroviral transfection into the cell of choice. One non-limiting method of accomplishing this is described as follows. On Day 1, $3 \times 10^6$ cells of the packaging cell line (293 gp) are seeded into a T175 flask. On the second day, two tubes, one carrying 15 ug of library DNA+10 ug of envelope plasmid (pCMV-VSV.G-bpa)+1.5 ml DMEM (serum free), the second carrying 100 ul of LipofectAMINE (Gibco BRL)+1.5 ml DMEM (serum free) are mixed and left at room temperature for 30 minutes. Subsequently, the two tubes are mixed together along with 17 ml of serum free DMEM. This cocktail is referred to as the "transfection mix." Previously plated 293 gp cells are then gently washed with serum free media and exposed to 20 ml of the transfection mix for 4 hours at 37° C. Following this period, the transfection mix can be removed and the cells are incubated with complete DMEM (10% serum) for a period of 72 hours at 37° C. On Day 4 or 5, the media (now referred to as "viral supernatant") overlying the 293 gp cells is collected, filtered through a $0.45\mu$ filter and frozen down in at −80° C.

As an alternative to the LipofectAMINE method of retroviral DNA packaging, a second protocol, referred to herein as the "$CaCl_2$ Method," can be used to package retroviral sequences. In this method, $5 \times 10^6$ cells of the packaging cell line (293 gp) are seeded into a 15 cm$^2$ flask on Day 1. On the following day, the media is replaced with 22.5 mls of modified DMEM. Subsequently, a single tube carrying 22.5 $\mu$g of retroviral library DNA and 22.5 $\mu$g of envelope expression plasmid (pCMV-VSV.G-bpa) is brought to 400 $\mu$l with $dH_2O$, to which is added 100 $\mu$l of $CaCl_2$ (2.5M) and 500 $\mu$l of BBS (dropwise addition, 2×solution=50 mM, BES (N,N-bis(2-hydroxyethyl)-2-aminoethane-sulfonic acid), 280 mM NaCl, 1.5 mM $Na_2HPO_4$, pH 6.95). After allowing this retroviral mixture to sit at room temperature for 5–10 minutes, i.e. is added to the 293 gp cells in a dropwise fashion, and the cells are then incubated at 37° C. (3% $CO_2$) for 16–24 hours. The media is then replaced and the cells are allowed to incubate for an additional 48–72 hours at 37° C. At that time, the media containing the viral particles is then collected, filtered through a $0.45\mu$ filter and frozen down at −80° C.

To infect the cell line or primary cells of interest, the selected target cells (e.g. HT29, SW620) are plated out at a density of approximately $1.5 \times 10^6$ cells per T175 flask. On the following day (Day 1), the library supernatant is added directly to the media (10–30% total volume) along with 4 $\mu$g/ml polybrene and allowed to incubate overnight. On Days 2 and Day 3, the supernatant is removed and replaced with fresh media. Floater cell populations are then collected on Days 3–5.

E. Recovery of Cytotoxic Sequences from Dead and/or Dying Cells.

In order to identify cytotoxic agents or substances which cause cell death, those agents (or the DNA sequences that encode them) are recovered from dead and/or dying cells.

Briefly, PCR is used to rescue and amplify DNA sequences encoding cytotoxic agents from non-viable cells. McPherson, M. J. et al., "PCR 2. A practical approach." Oxford University Press (1995). To compare the sensitivity of PCR on dead cells with that of viable cells, HT29 cells carrying a constitutive GFP encoding retroviral insert (pVT324) were induced to undergo apoptosis/necrosis using puromycin (2 $\mu$g/ml). After several days, floater cells were collected and stained with PI to allow selective identification and recovery of cells that had lost membrane integrity. Using flow cytometry, PI$^+$ (dead) cells were sorted directly into PCR tubes containing 25 $\mu$l of cell lysis buffer (50 mM KCl, 10 mM Tris-HCl, pH 8.0, 0.5% Tween-20, 0.5% Triton X-100, 2 mM $MgCl_2$, 1U/$\mu$l Proteinase K) and incubated at 1) 60° C. for 2 hours and 2) 95° C. for 10 minutes. Subsequently, 25 $\mu$l of the stock PCR reaction mix (50 mM KCl , 10 mM Tris-HCl pH 8.0, 400 uM dNTP's, 2 mM $MgCl_2$) was added to each tube and PCR was carried out using primers (0.4 uM) specific for amplification of the retroviral GFP construct (OVT131, 5'GACCTTCGGCGTC-CAGTGCTTCAG (SEQ ID NO: 12); OVT179, (5'AGCTAGCTTGCCAAACC TACA) (SEQ ID NO: 13). As a control, live cells (negative for PI uptake) from an untreated culture were also sorted and used for PCR. Results show that genomic DNA present in PI positive cells was clearly able to act as a suitable template for PCR amplification (FIG. 7). Amplification of the GFP product from dead cells did not appear altered in size or quantity compared to the product amplified from live cells.

Figure 8:
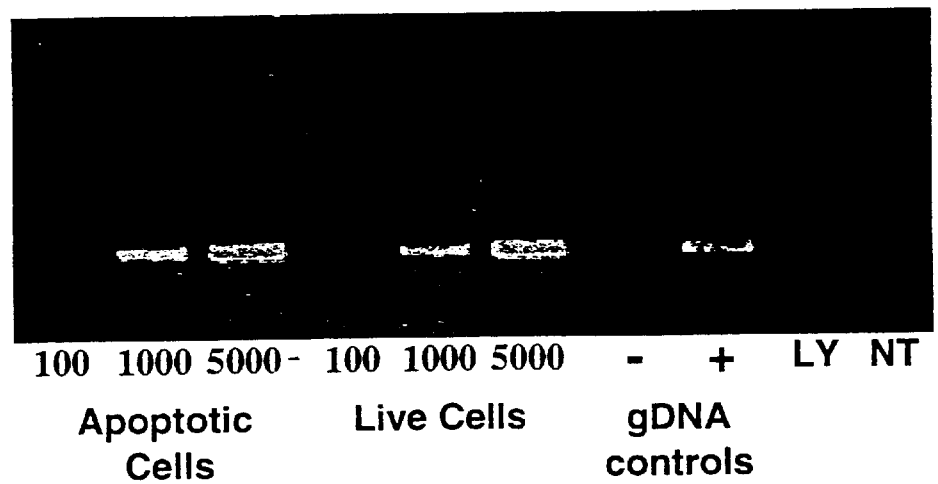
FIG. 8 is a gel comparing the PCR amplification of apoptotic cells, live cells and gDNA controls.

Cells that are positive for PI uptake may either be necrotic, or be in the late stages of apoptosis. In order to address specifically the question of whether DNA recovered from cells undergoing apoptosis can serve as a good template for PCR, the following experiment was performed. HT29 cells containing a retroviral construct that constitutively expresses GFP (pVT324) were treated with sulindac sulfide to induce apoptosis. After 48 hours of treatment, the majority of the cells had detached from the dish and showed typical apoptotic morphology (condensed nuclei). Apoptotic cells were counted into PCR tubes and PCR was carried out using primers specific for the amplification of the retroviral GFP construct. Live cells from an untreated culture were used as PCR controls. There was no apparent difference in amplification of the GFP product from apoptotic cells when compared to live cells (FIG. 8). Thus DNA recovered from cells undergoing either necrotic or apoptotic cell death can serve as an effective template for PCR amplification and construction of sublibraries.

Example Four

Negative Selection in HT29 Colon Cancer Cells

Twenty T175 flasks were seeded with $2.2 \times 10^6$ HT29 cells/flask in McCoy's 5A media (Gibco BRL) modified with 10% FBS. On Day 1, each flask was infected (4 $\mu$g/ml polybrene, 50% volume) with a retroviral supernatant containing a commercially obtained brain cDNA library ("Example Three" above). On Day 2 the media was changed. On Day 3 both the floater and adherent cell populations were collected (separately) from the twenty flasks. Approximately 652,500 floaters were isolated from a theoretical background of $4.2 \times 10^7$ adherents (1.5% floaters) and frozen down for future studies. Using the fluorescent properties of GFP as an indicator of infection, FACS analysis indicated that 76% of the viable cells were infected with the retroviral library. Additional floater cells were then collected Day 5, where the collection and counting procedures were repeated and some $7.8 \times 10^6$ floaters and $7.6 \times 10^8$ adherents were counted (1.03% floaters). The viable cell population was again scanned by FACS and the infection rate (GFP+) was found to 88%. The floater populations of Days 3 and 5 were then combined and readied for a genomic DNA prep using a QIAamp kit (Qiagen) following standard procedures. Briefly, some 9×10⁶ floater cells in PBS were lysed to release gDNA. This material was passed over a QIAamp column that was then washed several times to remove protein and RNA contaminants. Twenty-seven micrograms of genomic DNA were then eluted from the columns with dH₂O and treated with RNAse A to eliminate any RNA contamination. This gDNA was then subjected to PCR procedures to amplify the library sequences encoded therein. Briefly, the above gDNA aliquot was divided into 27×1 µg samples, for use as templates for PCR using the oligonucleotides OVT 800 (5'GCCGCCGGGA TCACTCTC) (SEQ ID NO: 14) and OVT 1211 (5'GCTAGCTTGC CAAACCTACAGGTGGGG) (SEQ ID NO: 15) (PCR conditions: 95° C., 30 seconds; 95° C., 15 seconds; 63° C., 30 seconds; 72° C., 3 minutes, cycle to "Step 2" twenty four times; 72° C., 5 minutes The resulting PCR products were then divided into 5 pools, and each pool was then purified using QIAquick (Qiagen), digested with EcoRI and XhoI, and then directionally ligated into the original retroviral vector (pVT340). This material was then transformed into electrocompetent bacterial cells (DH10B, Gibco BRL) and plated out on LB-amp plates to create five distinct sublibraries. Each library was subsequently grown in liquid culture (LB+ampicillin) and processed (Qiagen Maxi Prep) to yield material for the second round of packaging in 293 gp cells (see above). The resulting viral supernatants were then reinfected into naïve HT29 cells (1×10⁶ cells per flask, three flasks per sublibrary) to begin the second round of negative selection. Round two and all subsequent rounds of the negative selection differ from Round 1 in that a) only single infections were performed and b) floater cells from Day 3 and Day 5 from each sublibrary were pooled together. Repeated cycling in this fashion yields library clones whose expression results in cell death.

TABLE 2

Percent Floaters

| | Mock infected | 324 | Pool 1 | Pool 2 | Pool 3 | Pool 4 | Pool 5 |
|---|---|---|---|---|---|---|---|
| Cycle 2 | 0.6 | 0.7 | 1.1 | 0.9 | 1.1 | 1.1 | 1.1 |
| Cycle 3 | 1.0 | 0.4 | 2.0 | 1.1 | 2.1 | 1.5 | 1.2 |
| Cycle 4 | 0.9 | — | 2.9 | 2.8 | 4.3 | 2.3 | 3.6 |
| Cycle 5 | 0.7 | 0.6 | 3.2 | 4.4 | 9.0 | 3.8 | 5.5 |
| Cycle 6 | 1.2 | 1.3 | 12.0 | 11.0 | 14.0 | 11.0 | 12.0 |

Results from six consecutive cycles of the negative selections are shown in Table 2, above, and are summarized as follows. Both mock infected cells and pVT324 control vector cells consistently show 1% (or less) floaters in the media. In contrast, all five pools show a steady increase in the percent floater population over the course of the cycling with Pool 3 showing the greatest level of enrichment with 14% floaters in cycle six. This data demonstrates successful enrichment for perturbagen sequences that increase the frequency of dead and/or dying HT29 cells.

In addition to cycling these library sequences (obtained as described above) through an additional round of negative selections, 50 clones were taken from each of the Cycle 5, day five pools for sequence analysis. Two of these clones were found to encode portions of BID (BH3 Interacting Domain Death Agonist, Gene Bank Accession #AF042083), a known component of the apoptotic pathway. Both of the BID clones obtained from these negative selections encode N-terminal truncations of the native protein (BID Clone #1 encodes amino acids 33–195, BID Clone #2 encodes amino acids 76–195, See FIG. 9). BID clone #1 was reintroduced into fresh, naive HT29 cells and floater rates were compared with cells that had been mock infected or infected with the control vector, pVT324. Both controls exhibited low background floater rates of less than 1.5%. In contrast, HT29 cells infected with BID clone #1 exhibited roughly 18% floaters. In a similar experiment, BID clone #1 was introduced into HuVECs (Human Umbilical Vein Endothelial Cells, Clonetics/Biowhittaker) and cell viability was followed over the course of 16 hours. While control cells gave a background of 1% cell death at the 16 hour time point, 80% of the cells in the BID clone #1-infected culture died during the same period of time.

Figure 10:
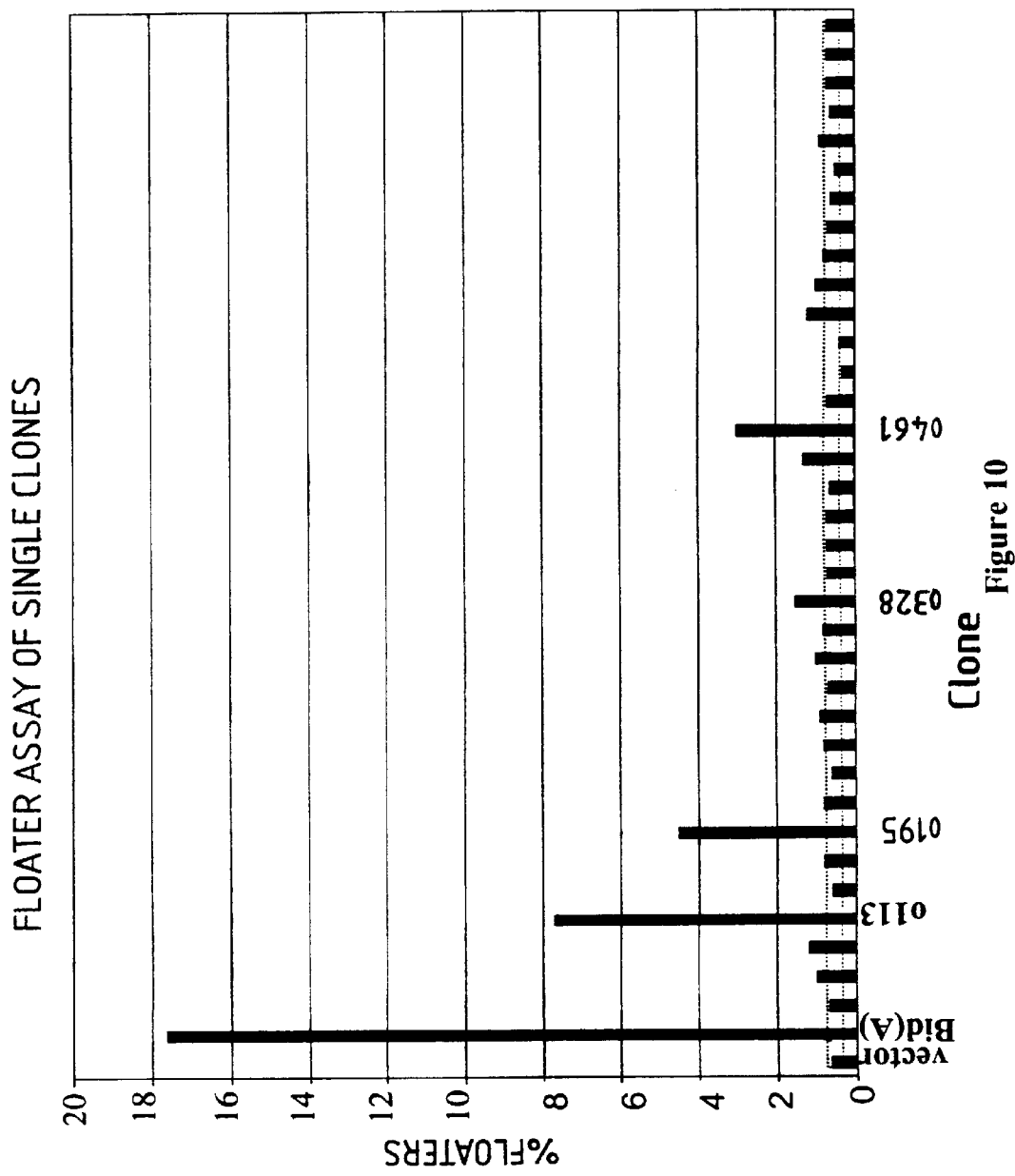
FIG. 10 depicts the analysis of clones from Sort VI of the HT29 floater assay described herein. Thirty six clones picked at random were tested in the HT29 floater assay. Five clones (BID, 0113, 0195, 0328, and 0461) showed increased levels of floaters that were statistically significant relative to background.

In addition to BID clones #1 and #2, four new cytotoxic agents have been identified from 36 clones picked at random (Sort VI). All four clones (0113, 0195, 0328, and 0461) give heightened levels of floaters in the HT29 floater assay. (FIG. 10). Weaker cytotoxic agents (e.g. 0328 and 0461) give floater rates of 2–3% (respectively) while the more moderate cytotoxic agents (0195 and 0113) induce between 4.5–7.5% floaters. The sequences of these agents are shown in FIG. 9.

Example Five Negative Selection in SW620 Colon Cancer Cells

Figure 11:
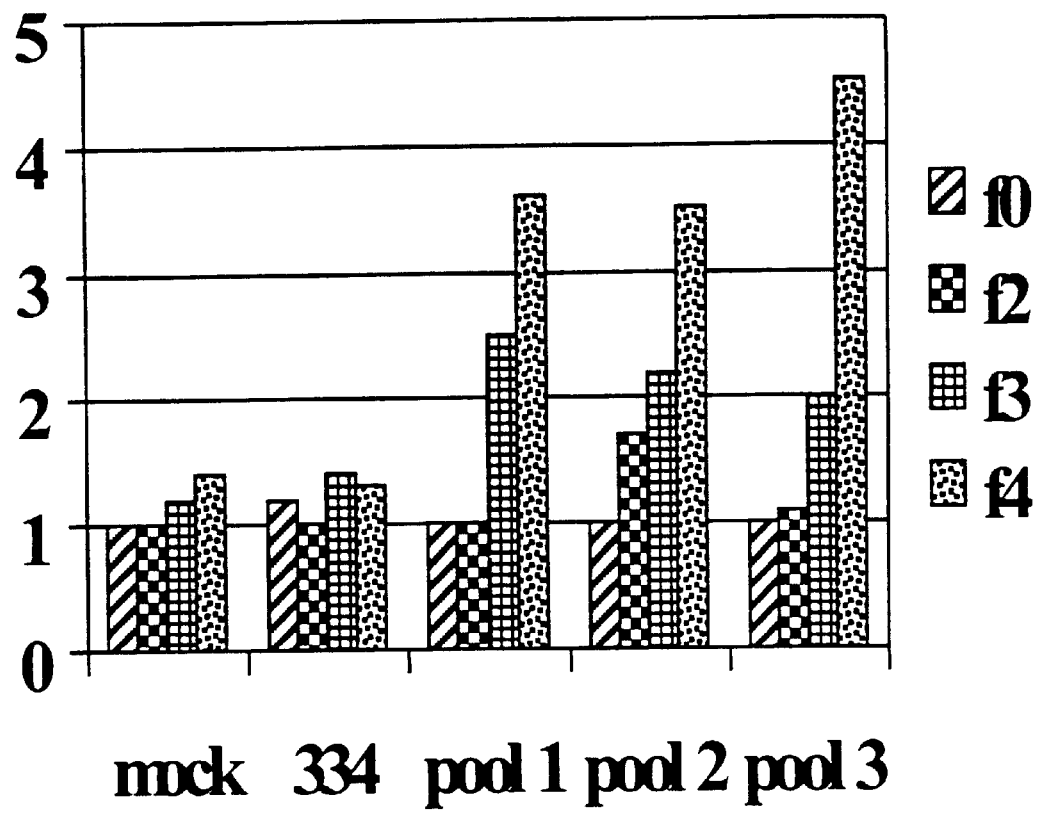
FIG. 11 is a bar graph depicting the floater rates in SW620 cells at F0 (starting library), F2 (after one collection and one sort), F3 (after one collection and two sorts) and F4 (after one collection, three sorts), wherein SW620 cells were infected with the random peptide perturbagen library and taken through several cycles of the negative selection described herein. Floater rate percentages were calculated at each step and compared with mock infected and pVT334 infected controls.
Figure 12:
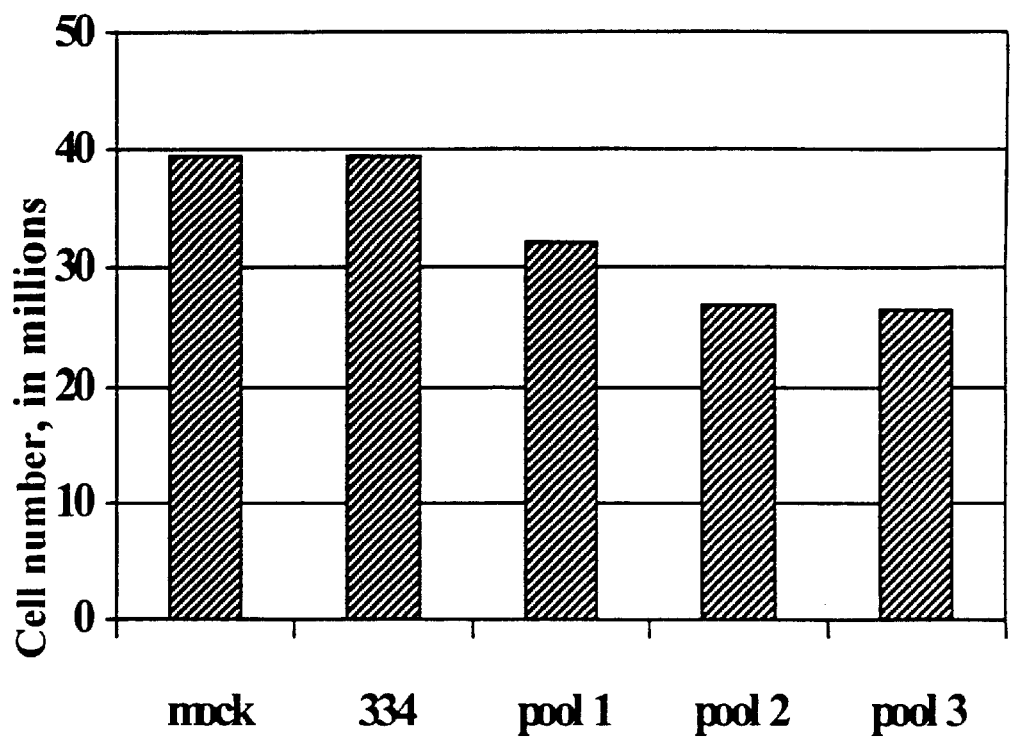
FIG. 12 is a bar graph depicting cell number observations for the SW620 cells of the negative selection described herein. Equal numbers of control (i.e., mock infected and pVT334-infected) cells and F3 (peptide library infected) cells were plated in T75 flasks. On day 5, the flasks were washed and trypsinized and the total number of adherent cells was determined.

In a negative selection very similar to the HT29 screen described above, twenty flasks of SW620 colon cancer cells were plated (3 million cells/flask) and infected with one of two putative cytotoxic sequence-encoding libraries. The first library was made from random primed placental cDNA inserted into the MFG vector. The second library of putative cytotoxic agents was a random oligonucleotide library inserted into an internal site (insertion site 6, pVT27) of GFP (pVT 334, see Abedi et al. 1998). Following infection of these libraries into the SW620 cell line, floaters were collected at 48 and 96 hour time points (Days 3 and 5). These cells were then treated with propidium iodide (see above) and PI⁺ cells were sorted out by FACS. PI⁺ floater cells from both time points were then divided into three separate pools for a genomic DNA preparation. Subsequently PCR was used to amplify and recover the relevant perturbagen encoding sequences. Two unique sets of primers were used for PCR amplification; for the random primed placental library, OVT 1136 (5'GGATCACTCTCGGCATGGACGAG) (SEQ ID NO: 16) and OVT 1137 (5'ATCCGCGGCC GCGGCCATAATGGCC) (SEQ ID NO: 17) were used. For the random peptide (oligo) library, OVT 777 (5'GACTGCCATGGTGAGCAAGGGC) (SEQ ID NO: 18) and OVT144 (5'GCCGTCCTCGATGTTG TGGCGGAT) (SEQ ID NO: 19) were used. Results show that after performing four cycles of the infection and collection procedures (F4) in SW620 cells infected with the peptide library, the background level of Day 5 floater cells rose from approximately 1% in the original library to (on an average), 3.9% (FIG. 11). At the same time, background levels of floaters in the mock and pVT334 remained low at 1.35%. While the increase in background floater level was not accompanied with a concomitant increase in PI⁺ cells in the floater population, a decrease in the total cell number was observed over the course of the selection process, suggesting that one or more library sequence(s) that affect cell growth rates/cell viability are being enriched (FIG. 12). These potential cytotoxic agents (as well as those from earlier rounds of selection using the random primed placental library) are then reintroduced into naive SW620 cells and cycled again. Following 4–6 rounds of cycling, individual library inserts are sequenced and validated for cytotoxic activity.

Example Six

Negative Selection in T47D Metastatic Mammary Epithelial Cells

An additional example of floater assays involves the cell line T47D (ATCC) which is derived from a metastatic mammary epithelial cell tumor. T47D was chosen for study primarily due to the relatively low floater rate that it displays, and its ease of infection with retroviral based vectors.

To determine floater rates for the T47D cell line, cells were plated to 20% confluency in T175 tissue culture flasks (roughly $5\times10^5$ cells/flask) and the number of floaters as a percentage of total cells (adherent+floaters) was ascertained. Floater rates for T47D cells were determined to be 0.5% over a 3–5 day period in culture. In addition, 70% of the floater cells were observed to be dead as judged by trypan blue staining ("Handbook of Fluorescent Probes and Research Chemicals" Haugland, R. P., Molecular Probes). In contrast, less than one percent of the adherent cells were found to be dead using the same staining methods. Thus by harvesting floater cells from a T47D culture, at least 30% of the total number of dead and or dying cells are obtained. As the infection rate of this cell line with the pVT324 retroviral vector was observed to be approximately 90%, the T47D cell line thus was suitable for negative selections.

The T47D cell line is then utilized for a conditional negative selection—i.e., a selection in which cytotoxic agents that act under a unique set of conditions are identified. In this non-limiting Example, library sequences that enhance the sensitivity of T47D cells to the chemotherapeutic drug, camptothecin (an inhibitor of topoisomerase II), are selected as follows.

Figure 13:
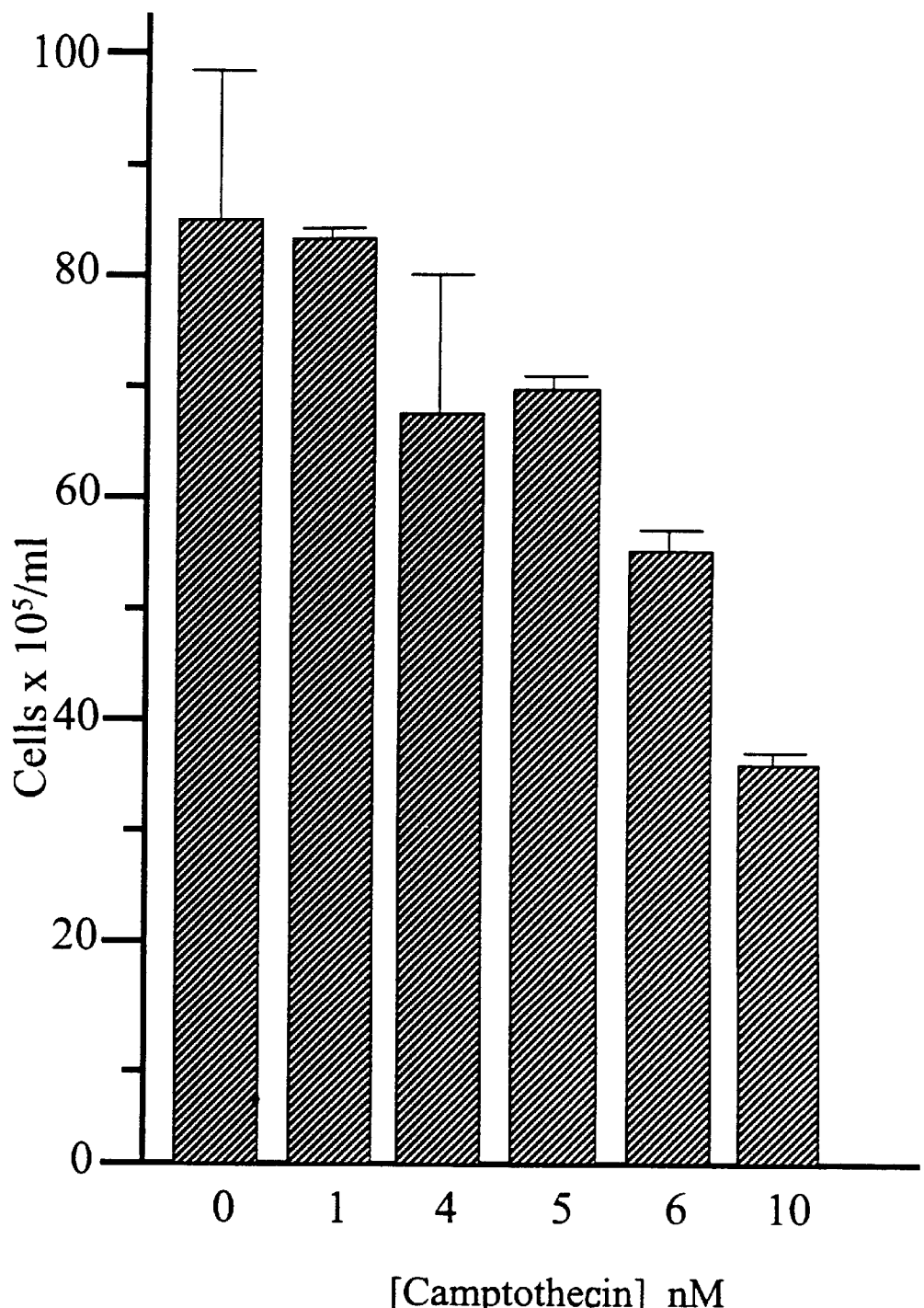
FIG. 13 is a kill curve for varying amounts of camptothecin in T47D cells.

Initially, a maximal concentration of camptothecin that failed to increase T47D cell floater rate was determined as follows. Approximately 250,000 cells were seeded into each well of a six well plate. Cells were then grown in media containing camptothecin of varying concentrations (0–10 uM). After 5 days, the number of cells remaining in each of the camptothecin-treated wells was compared with untreated controls. From these experiments, it was determined that camptothecin concentrations ranging from 1–4 nM had no effect on T47D cell number over the course of the 5 days of treatment. Treatment of cells with concentrations greater than 4 nM resulted in a decrease in cell number relative to the untreated control (FIG. 13). As can be seen, cell number in the presence of 10 nM camptothecin was roughly one third that found in the untreated control, and virtually no cells remained adhered to the plate when exposed to camptothecin concentrations greater than 50 nM. These results suggest that T47D cells can tolerate camptothecin concentrations up to 4 nM without an adverse effect on either cell viability or division. In order to determine whether this level of treatment is concomitantly increasing the number of floaters in the population, several flasks are seeded with T47D cells and then treated with 1–4 nM concentrations of camptothecin. After a period of three to five days, the media is collected and the number of floater cells are counted and compared to the total number of cells in the flask (floaters+ adherents).

To perform a conditional negative selection involving T47D cells, the following experiments are performed. Cells are infected with either a retroviral-based cDNA or peptide expression library (See "Example Three") as described for HT29 colon cancer assay. Following infection, cells are treated with 4 nM camptothecin and floater cells are harvested over a 5 day period. As was described in "Example 5" and "Example 1B", additional enrichment of library inserts encoding cytotoxic agents can be achieved by including in this protocol a PI staining/recovery (FACS) step that enables the identification of dead and/or dying cells. Library inserts present in these floater cells are recovered by PCR, subcloned into a retroviral vector, and subsequently reintroduced into naïve T47D cells. Following this second infection, floater cells are again harvested over a five-day period in the presence of 4 nM camptothecin and the cycle is repeated. As was the case with the HT29 negative selection, repeated cycling in this manner should yield library clones whose expression results in cell death either in the presence or absence of camptothecin.

To identify the subset of library clones that cause cell death only in the presence of sub-toxic levels of camptothecin, one of two counterscreens is employed. First, the sub-library of inserts that cause cell death is introduced into T47D cells in the absence of camptothecin. Cells containing library clones that cause non-specific cell death will die, whereas clones that induce death only in the presence of camptothecin, will survive. To identify those clones that specifically increase the sensitivity of metastatic cells to camptothecin, a second counterselection is employed. Library inserts that cause camptothecin-specific death are introduced into primary mammary epithelial cell (Clonetics-Bio-Whittaker, Catalogue #cc-2551), in the presence of sub-toxic levels of camptothecin. Library inserts present in cells that survive this treatment are then recovered by PCR, subcloned into the original host retroviral vector, and analyzed. Through the use of these two counter selections, cytotoxic agents that specifically increase the sensitivity of metastatic breast epithelial cells to the chemotherapeutic agent camptothecin are identified.

Example 7

Negative Selections in HuVEC Cells

Figure 14A:
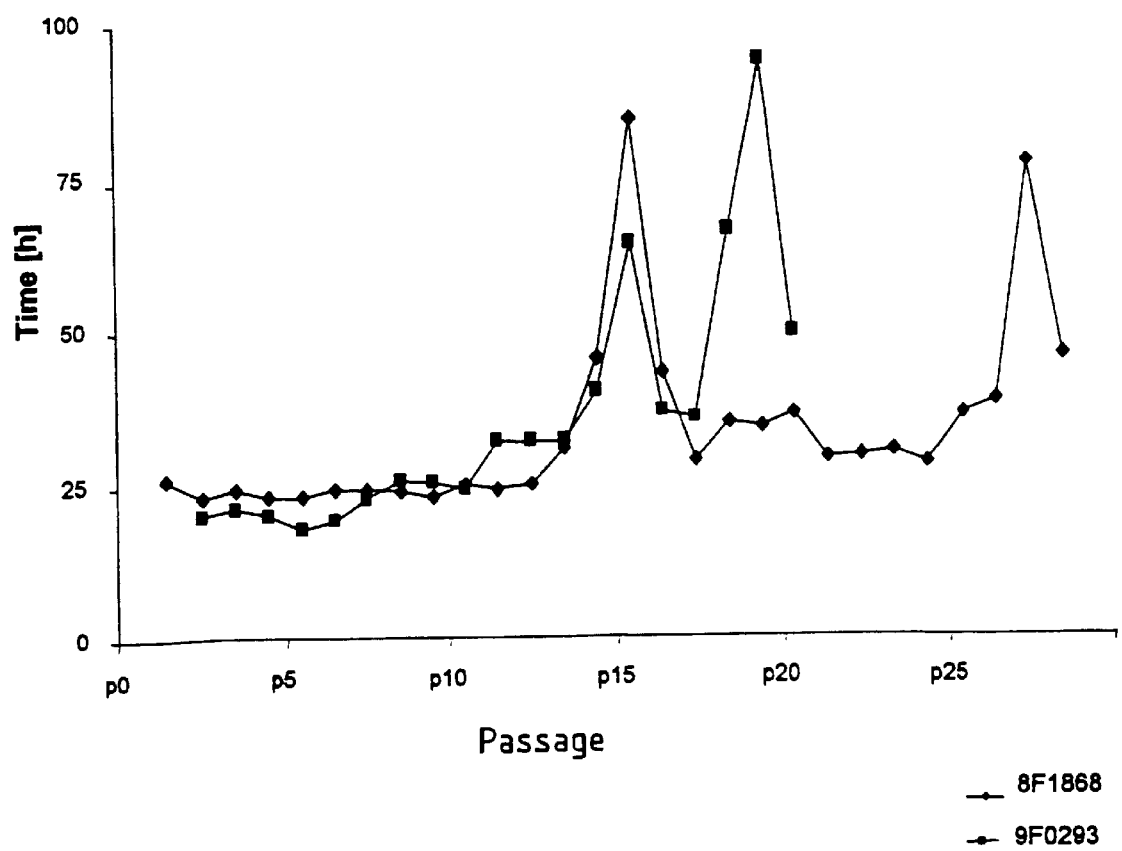
FIG. 14A and 14B show graphs comparing the doubling time and senescence of two HuVEC cell isolates, 8F1868 and 9F0293.
Figure 14B:
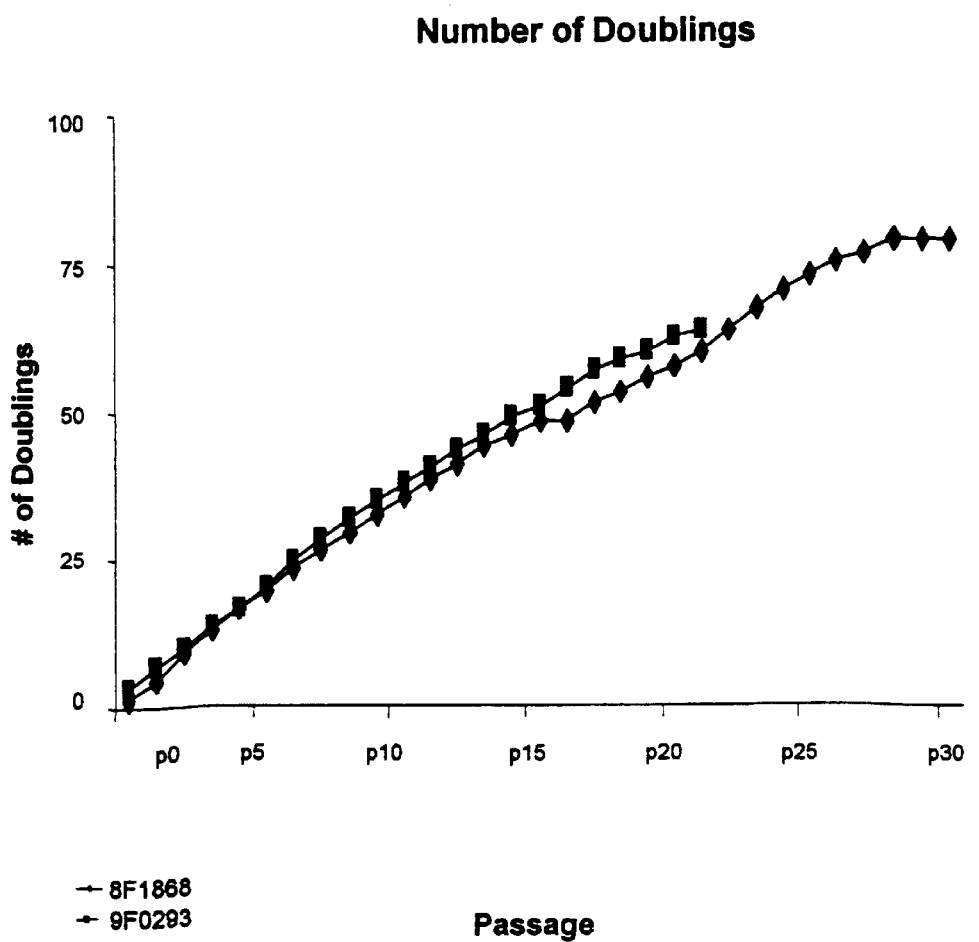

As an alternative to performing negative selections on transformed (immortalized) cells (e.g. HT29), protocols have been developed to apply the floater assay to primary cells. HuVECs (Human Umbilical Vein Endothelial Cells) are primary cells frequently used to pursue studies in angiogenesis. To prepare for negative selections in primary cells, two isolates of HuVECs, 8F1868 and 9F0293 (Clonetics/ Biowhittaker) were plated in EGM-2 media (Clonetics/ Biowhittaker) and observed over the course of several weeks to determine the doubling time and longevity of the cultures. Both lines exhibited a fairly consistent doubling period over the course of the first 10–12 passages (~24 hrs). The life span of 9F0293 was limited to twenty passages with later passages (>12) exhibiting both broad fluctuations in doubling time and an alteration in morphology from cobblestoned, epithelial-like cells to a more flattened, fibroblast-like morphology. In contrast, the 8F 1868 line had a life span that extended to 30 passages and showed a greater consistency in doubling time. Because these two cultures performed identically during the first six passages and because the proposed negative selections would take place during passage four, line 9F0293 was chosen for future negative (FIG. 14).

To assess the feasibility of using primary cell lines in negative selections, the 9F0293 line was tested for a) susceptibility to retroviral infection and b) the background percentage of floater cells. Three samples of an early passage of 9F0293 cells (control, mock infected, and infected) were plated at a density of $2\times10^5/15$ cm$^2$ plate and followed over the course of 120 hours. During that time the total cell number, doubling time, and floater ratios (calculated here as total # of floaters/total # of adherents) were recorded and compared. Cells were infected with pLIBEGFP (Clontech) and packaged using the $CaCl_2$ protocol described previously. Retroviral infection protocols used in these procedures included a 12 hour period of infection using an MOI (moiety of infection) of 2.0, and 4 ug/ml of polybrene.

Figure 15A:
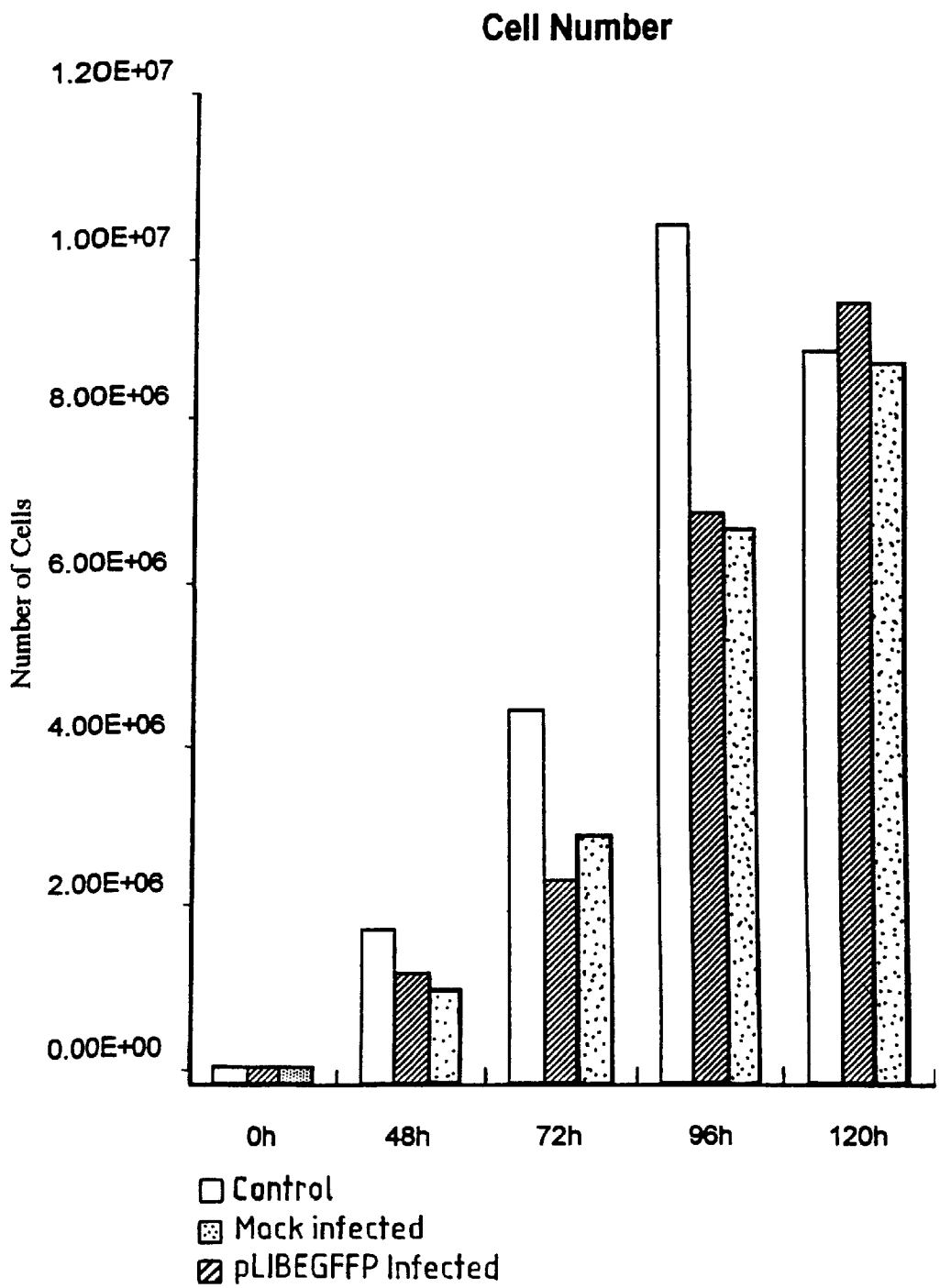
FIGS. 15A-C are bar graphs showing the effects of retroviral infection on cell number, doubling time and floater rate. HuVEC 9F0293 cells were infected with the pLIBEGFP vector and studied to determine the effects of retroviral infection and infection procedures on cell number, doubling time and floater rates. Doubling time is measured in hours. Floater rates are measured in percentages (number of floating cells/number of adherent cells).
Figure 15B:
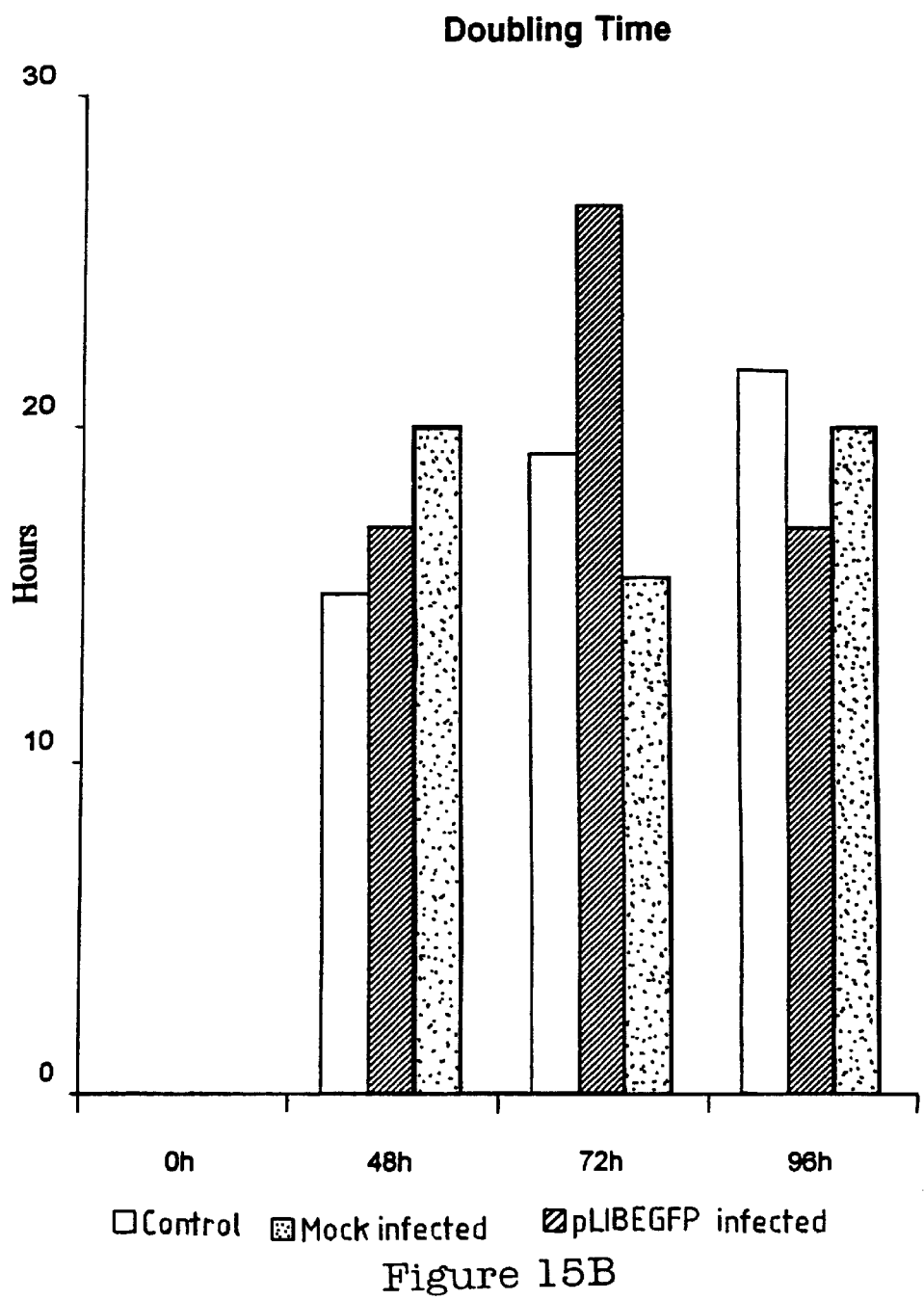
Figure 15C:
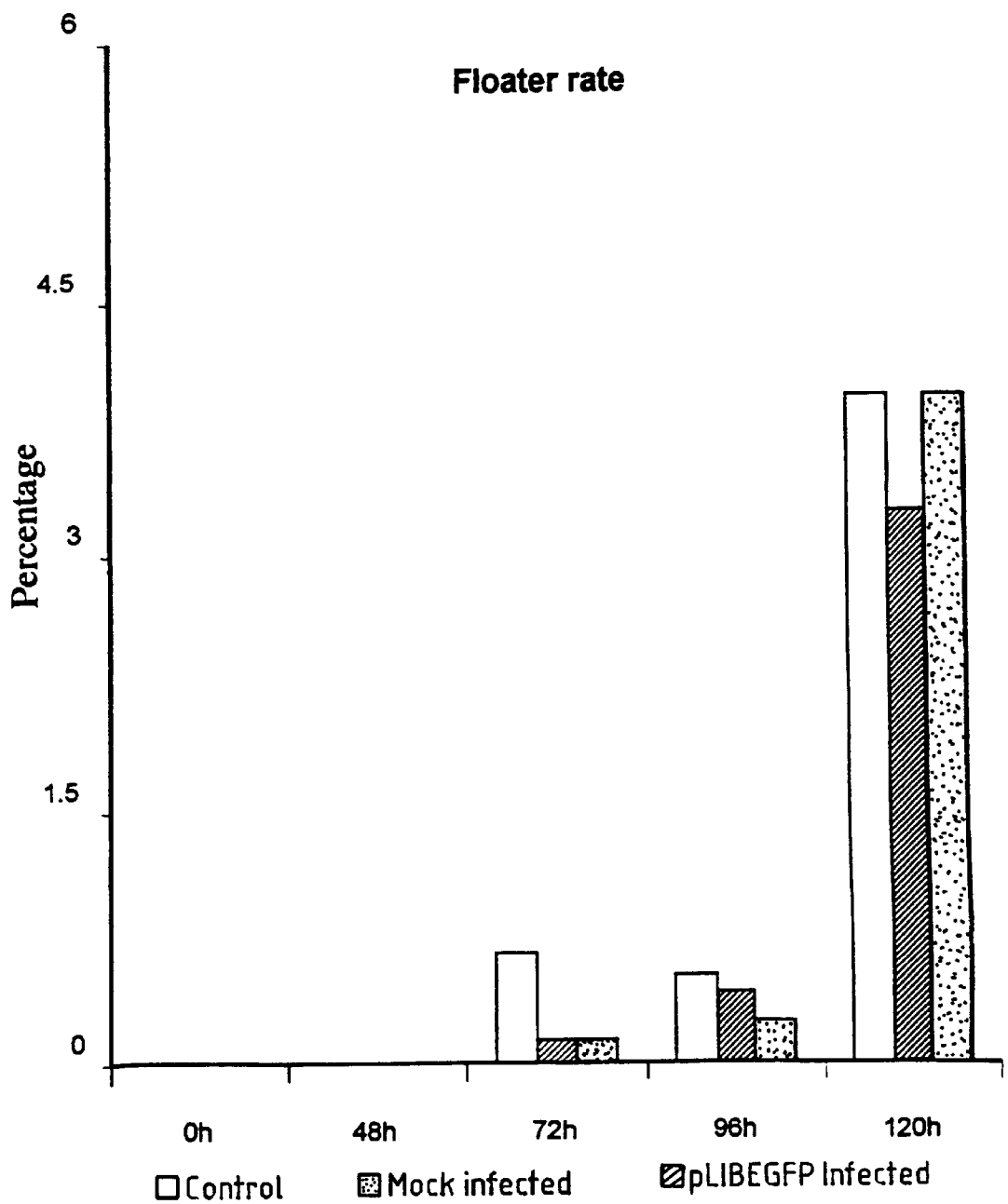

Results show that when compared to the controls, the infection procedure and presence of retrovirus altered the total cell number and doubling time of the 9F0293 line only slightly. In addition, at all points prior to 120 hours, floater ratios in all three scenarios were consistently below 1%. At 120 hours, cell cultures were confluent and floater ratios increased (3% or greater), an observation that is consistent with nearly all ammalian cell cultures studied thus far (FIG. 15). In addition, the 9F0293 line of HuVECs proved to be highly susceptible to retroviral infection, with the percentage of cells falling into the GFP$^+$ gate averaging between 70–80%.

Figure 16:
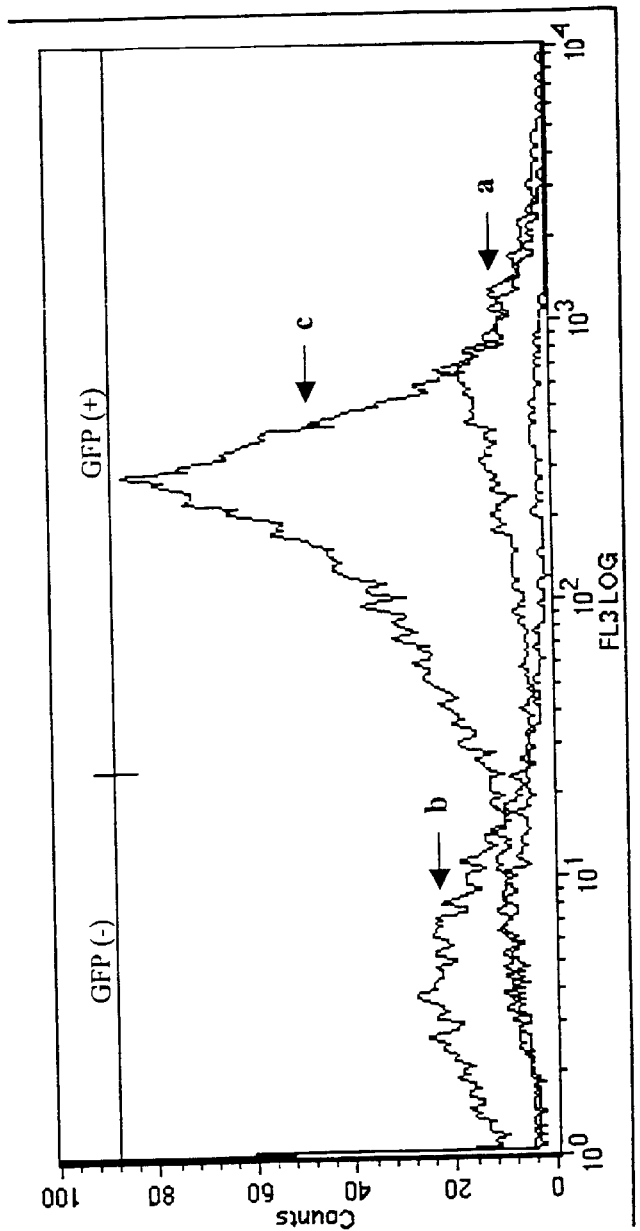
FIG. 16 is a FACS histogram depicting the time course of PI−/PI+ HuVECs in puromycin-treated cultures. 9F0293 cells were treated with puromycin (2 μg/ml) and followed over the course of 24 hours. Floater cells were collected at defined intervals and were treated with PI and subjected to FACS analysis to determine the percentage of dead and/or dying cells.

To determine the time course in which dead and/or dying HuVECs detach from the solid support in response to a cytotoxic agent, 9F0293 cells were plated and subsequently treated with puromycin (2 ug/ml). Both floater and adherent cell populations were then collected at varying times (t=4, 7, 9, 16, 20, and 24 hours) and analyzed to determine (a) the percent PI$^+$ cells in the floater population and (b) the fraction of cells which became floaters. The results of these experiments showed that the majority of HuVECs detached at the 16-hour time point and that 90–99% of the cells became floaters within 24 hours after addition of puromycin. The fraction of floaters that stained with PI (PI$^+$ population) increased with time. At early time points (4, 7, and 9 hours), PI$^-$ and PI$^+$ floater cells were in near equal numbers. By 20 hours, nearly all the floater cells fell into the PI$^+$ gate, suggesting HuVECs detach as PI$^-$ cells and then rapidly convert to the PI$^+$ phenotype (FIG. 16).

To identify cytotoxic agents that induce apoptosis/necrosis in HuVECs, 9F0293 cells are plated on a solid support (gelatine) and infected (MOI=2, 16 hr infection, 4 ug/ml polybrene) a retroviral-based library of inserts which use the backbone of pCLMFG (see "Example 3, Section B" above) or PLIB (Clontech) as the retroviral vector. Either random oligonucleotides inserted into the VT27 loop of GFP (see above, Abedi et. al. 1998), cDNA, or genomic DNA fused to the C-terminus of GFP (see "Example 3, Section B" above), are screened for cytotoxic agents." At 48 hr, 72 hr, and 96 hr time points post infection, floater cells are collected. Floaters from the two earliest collection points are pooled together (Pool 1). Floaters from the 96 hr time point form a separate pool (Pool 2). Genomic DNA prepared from each pool is then used to amplify the library inserts using standard PCR techniques (see above). The product from this reaction is then recloned into the appropriate retroviral vector, and reinfected into naive 9F0293 cells for subsequent rounds of screening and enrichment. In later rounds of screening (>4), individual perturbagen clones are isolated, reintroduced into HuVECs, and tested to determine if such library inserts increase the level of floater cells above the background floater rate observed in uninfected and mock infected cultures.

Library inserts found to be cytotoxic in HuVECs are then introduced into additional cell types to determine the cell or tissue-type specificity of the encoded agents. Specifically, the encoding cytotoxic agents are introduced into HT29, SW620, DLD-1, as well as other cell lines (both primary and genetically altered so as to be immortalized or transformed). The levels of cell death are monitored using any one of (but not limited to) the techniques described in "Example One".

Example 8

Identifying Agents that Overcome Multidrug Resistance

The present invention may be readily applied to identify agents that sensitize multidrug resistant (MDR) cancer lines to currently available chemotherapeutic agents. One non-limiting example is as follows.

Many MDR strains (e.g. LS513, LS1034) can be obtained through ATCC. Alternatively, MDR strains can be obtained by the following, non-limiting procedure.

Ten T75 flasks containing 2×10$^6$ HT29 cells/flask are subjected to a drug (e.g. taxol) at concentrations that induce 90–95% cell death. Following this treatment, the surviving cells are allowed to expand in normal media, whereupon they are subjected to elevated levels (e.g. 5×) of the drug. As a result of multiple cycles of killing, regrowth, and stepwise increases in drug concentrations, an HT29 MDR strain is evolved.

Prior to performing a screen for perturbagens that sensitize multidrug resistant (MDR) cancer lines to currently available chemotherapeutic agents, it is critical to first determine a sublethal concentration of the drug to be used in the studies. In this example, a "sublethal" dose is a concentration of a drug that is capable of killing an MDR$^-$ cell line, but has little or no effect on an MDR$^+$ line. In one non-limiting example of how a sublethal concentration can determined, killing curves are performed on both LS513 (an MDR$^+$ line) and several MDR$^-$ control lines. Specifically, 1×10$^6$ LS513 cells are plated in 15 cm$^2$ plates and allowed to adhere overnight. On the following day, taxol is added to the culture at a range of concentrations varying from 2 nM–500 uM. The cells are then cultured for an additional 2–7 days, whereupon the cell number and floater rates are compared. A sublethal concentration of taxol is then defined as a concentration of the drug that that kills greater than 50% of the MDR$^-$ (control) cells but induces less than 2% lethality in the LS513 line.

To identify sequences that disrupt the MDR phenotype, library inserts (either cDNA or random peptide based) are introduced into adherent MDR lines (e.g. LS513 and LS1034 colorectal carcinoma cell lines, ATCC) using the retroviral technology described above. These cells are then subjected to sublethal concentrations of chemotherapeutic drugs (e.g. taxol, adriamycin, vinblastine, actinomycin) and cultured over a period of two to seven days. As the majority of cells do not contain a library insert that will enable the drug to overcome or disrupt the mechanism of multidrug resistance (e.g. P-glycoprotein), these cells will continue to divide and remain adherent to the solid support. To identify library inserts that enhance the sensitivity of MDR cells to chemotherapeutics (essentially converting an MDR$^+$ line to MDR$^-$) floater cells are collected over the course of the experiment. Again, as described in previous sections, additional enrichment of cytotoxic perturbagens with these characteristics can be achieved by including in this protocol a PI staining/recovery (FACS) procedure that enables the identification and recovery of dead and/or dying cells. The sequence(s) are then recovered and amplified from floater cell genomic DNA preparations via PCR and recycled through an additional round(s) of selection to enrich for perturbagen sequences that disrupt the MDR phenotype.

To identify the subset of library clones that cause cell death only in the presence of sub-toxic levels of taxol, a counter screen is employed. The sub-library of inserts that cause cell death is introduced into LS513 cells in the absence of taxol. Cells containing library clones that cause non-specific cell death will die. whereas clones that induce death only in the presence of taxol will survive.

Figure 17:
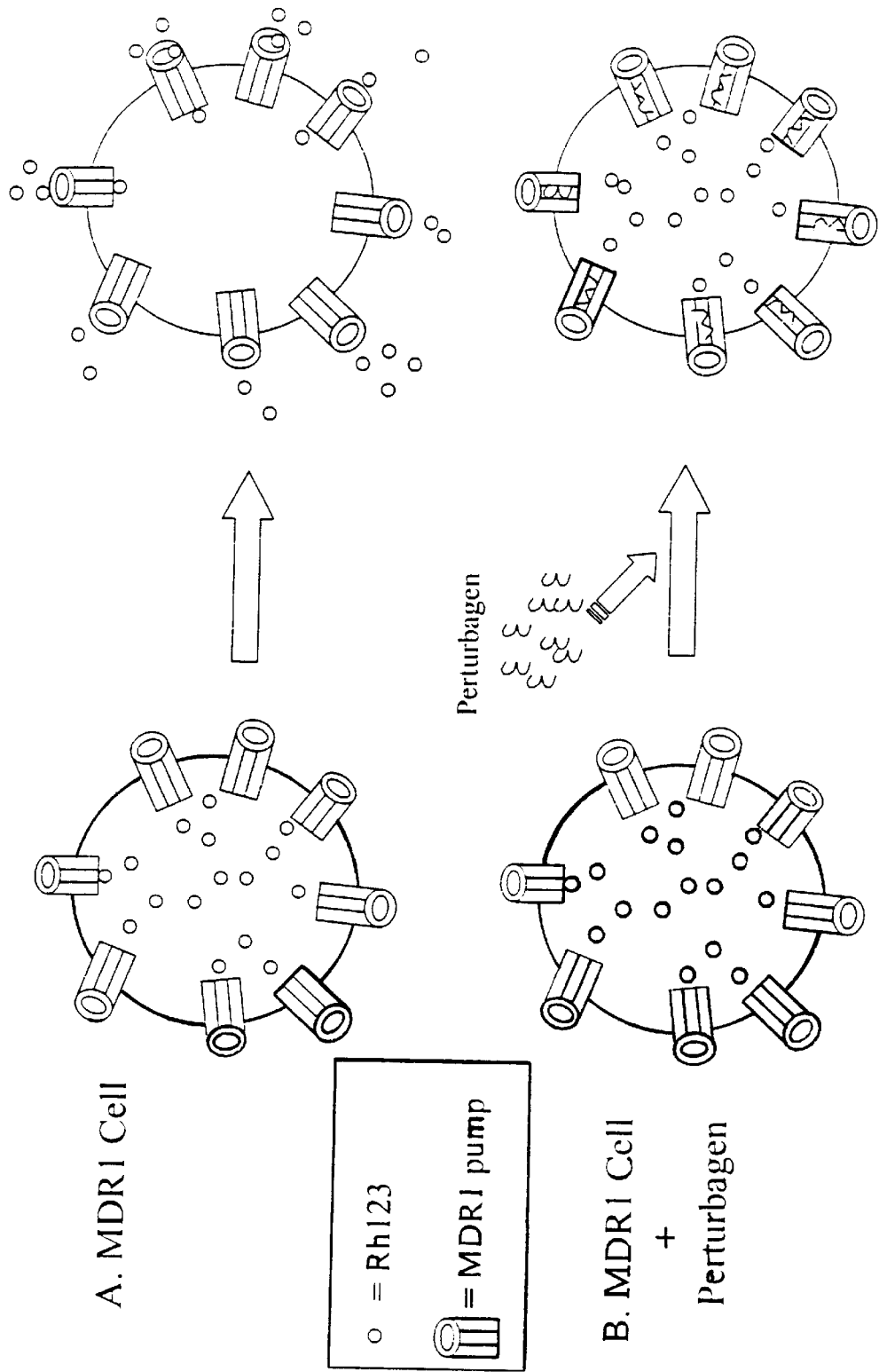
FIG. 17 is a diagrammatic representation of the P-glycoprotein pump-mediated extrusion of Rhodarnine 123 from an MDR1 cell, in the presence and absence of library inserts (referred to herein as "Perturbagens"). In an untransformed MDR1 cell, the P-glycoprotein actively pumps Rh23 out of the cell, causing the cells to be "dim." In the MDR1 cell bearing an active Perturbagen, the pumping action of P-glycoprotein is blocked or disrupted, and as a result, the cells retain Rh123 and remain "bright."
Figure 18A:
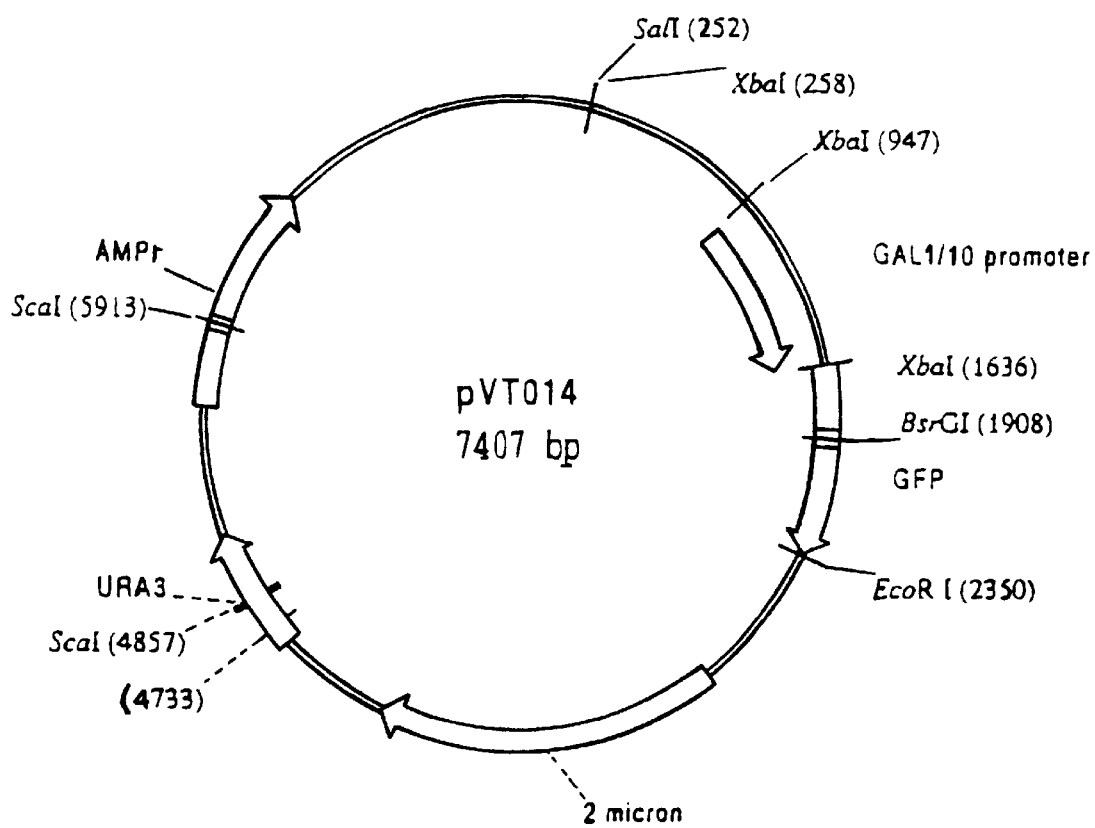
FIGS. 18A-F are diagrammatic representations of vectors referenced in the description of some embodiments of this invention.
Figure 18B:
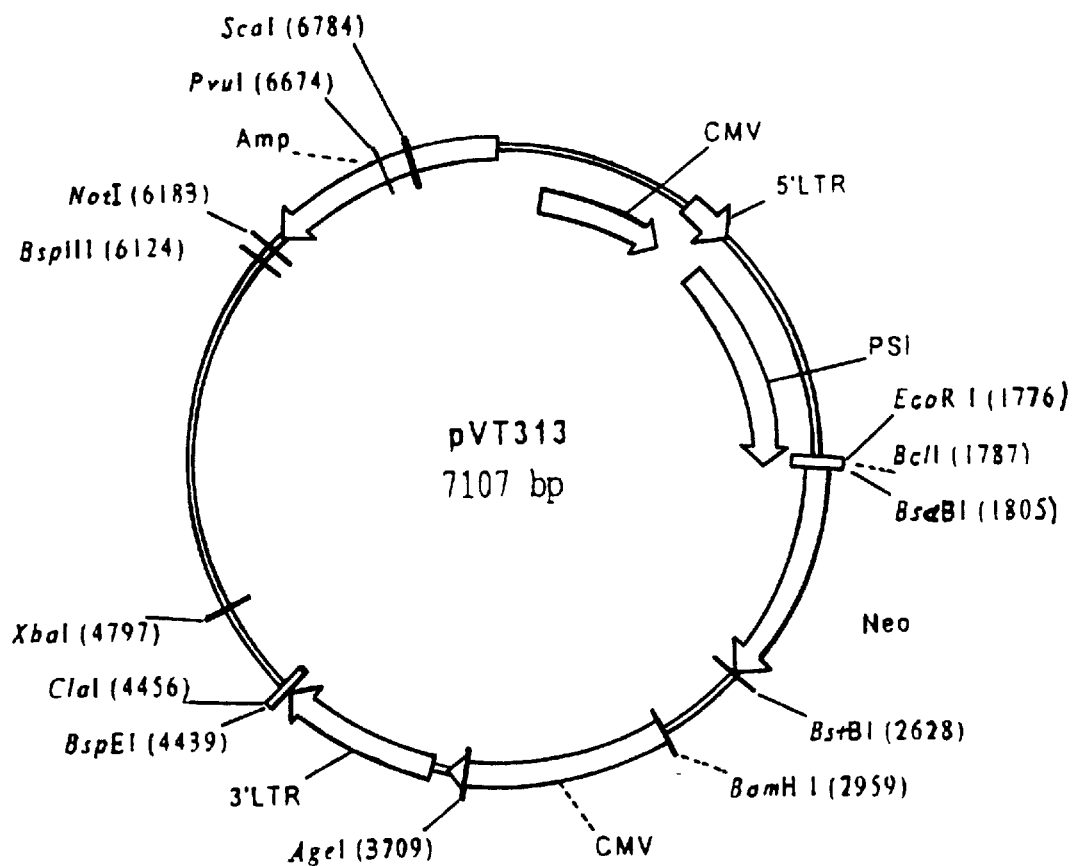
Figure 18C:
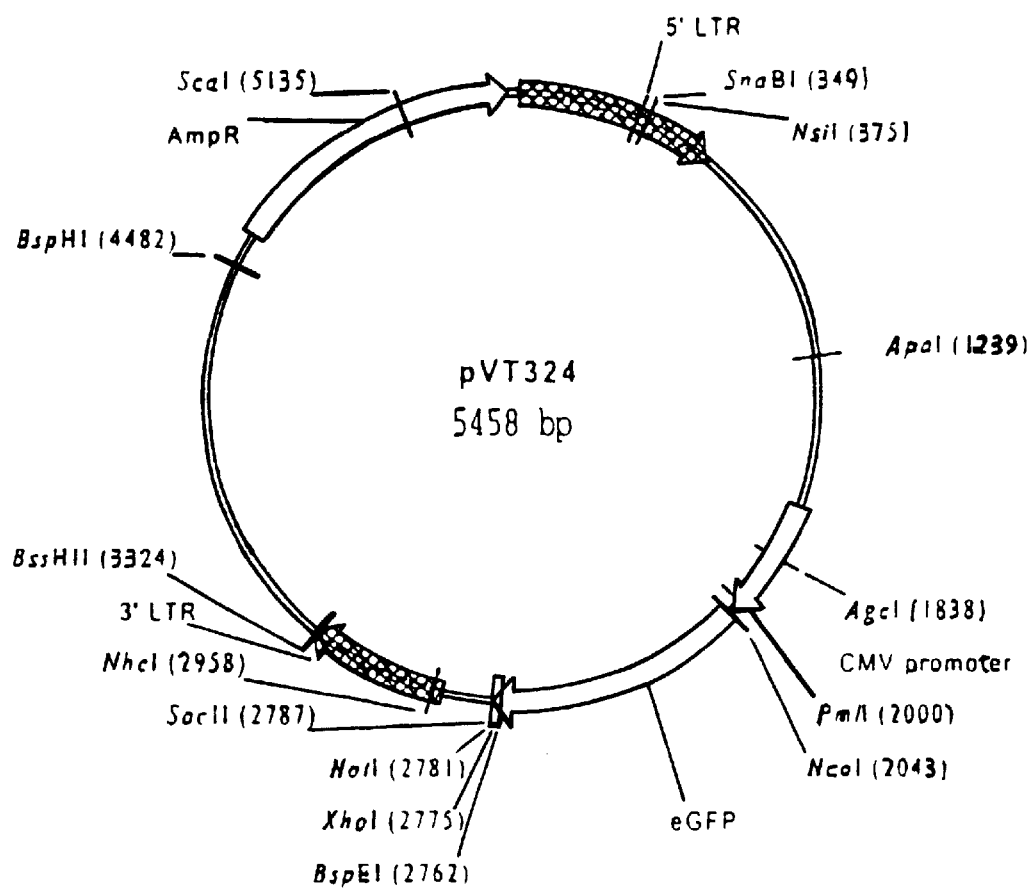
Figure 18D:
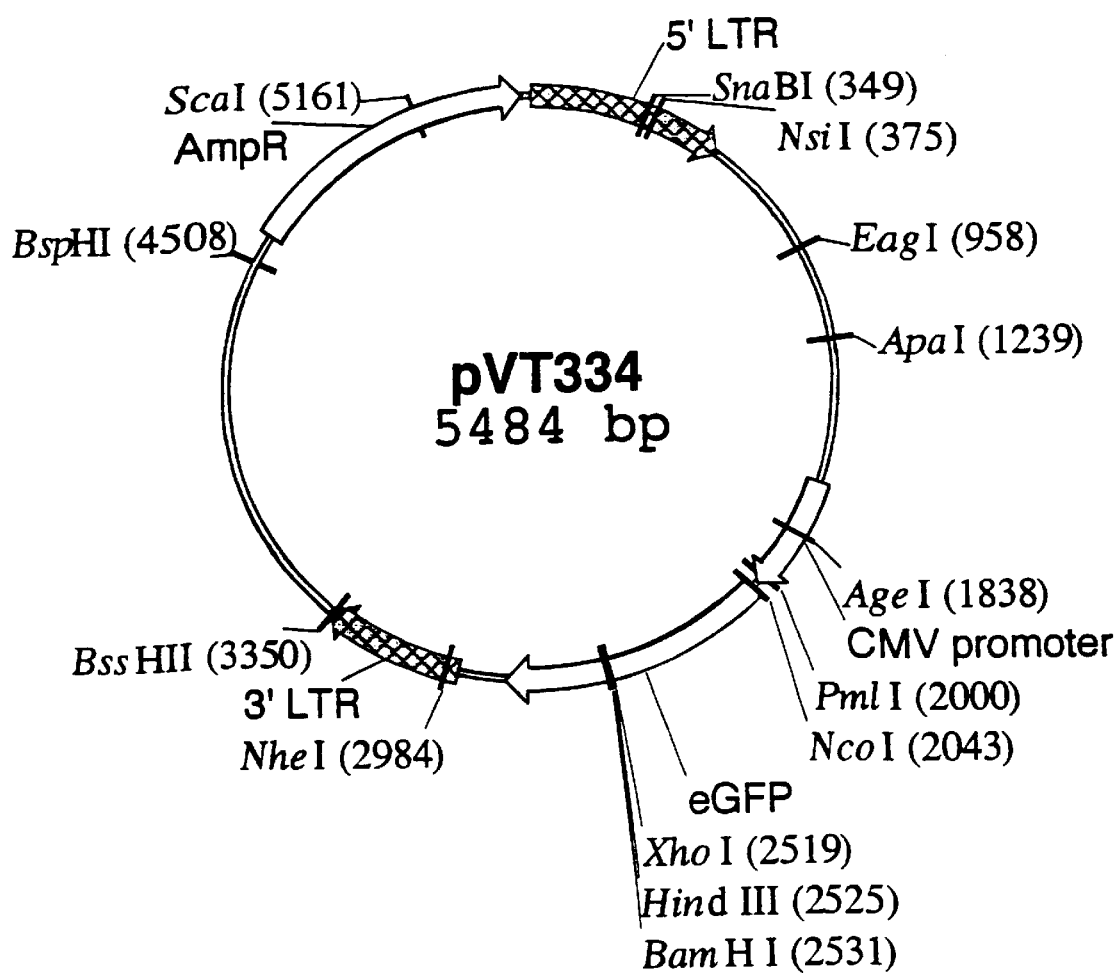
Figure 18E:
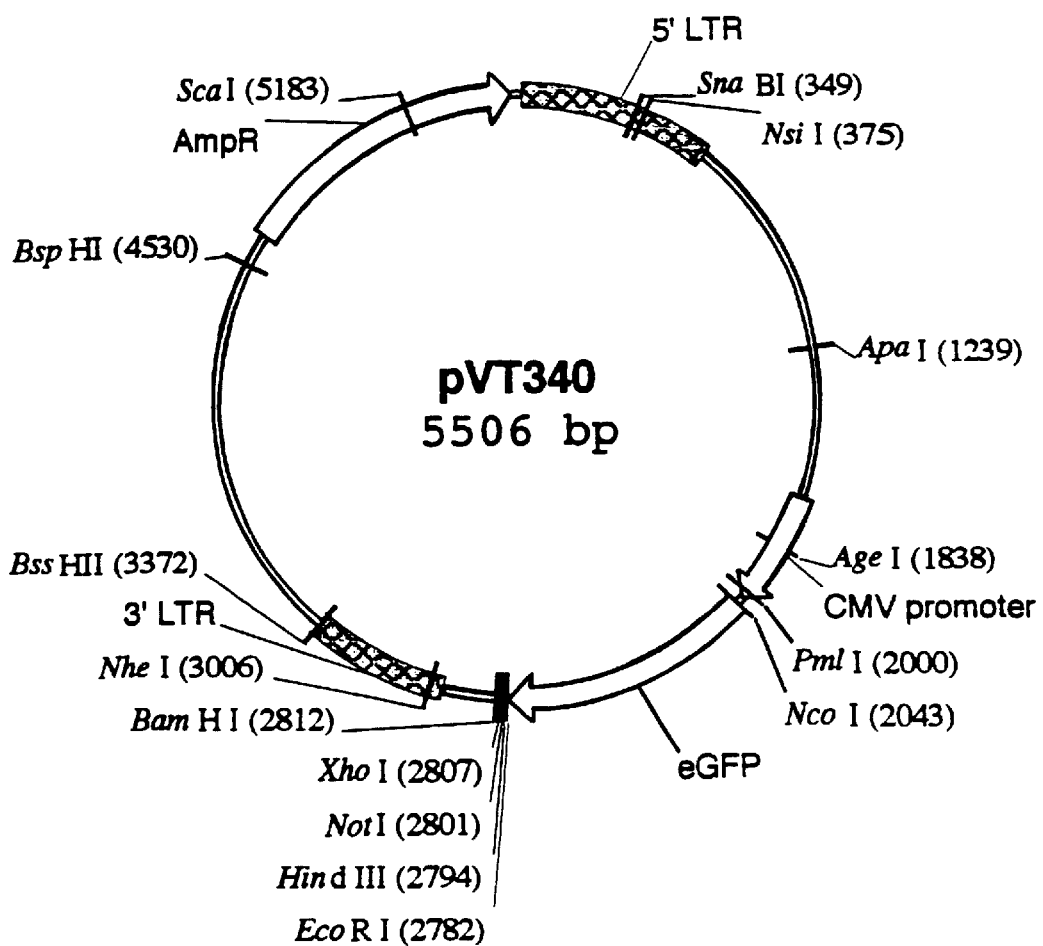
Figure 18F:
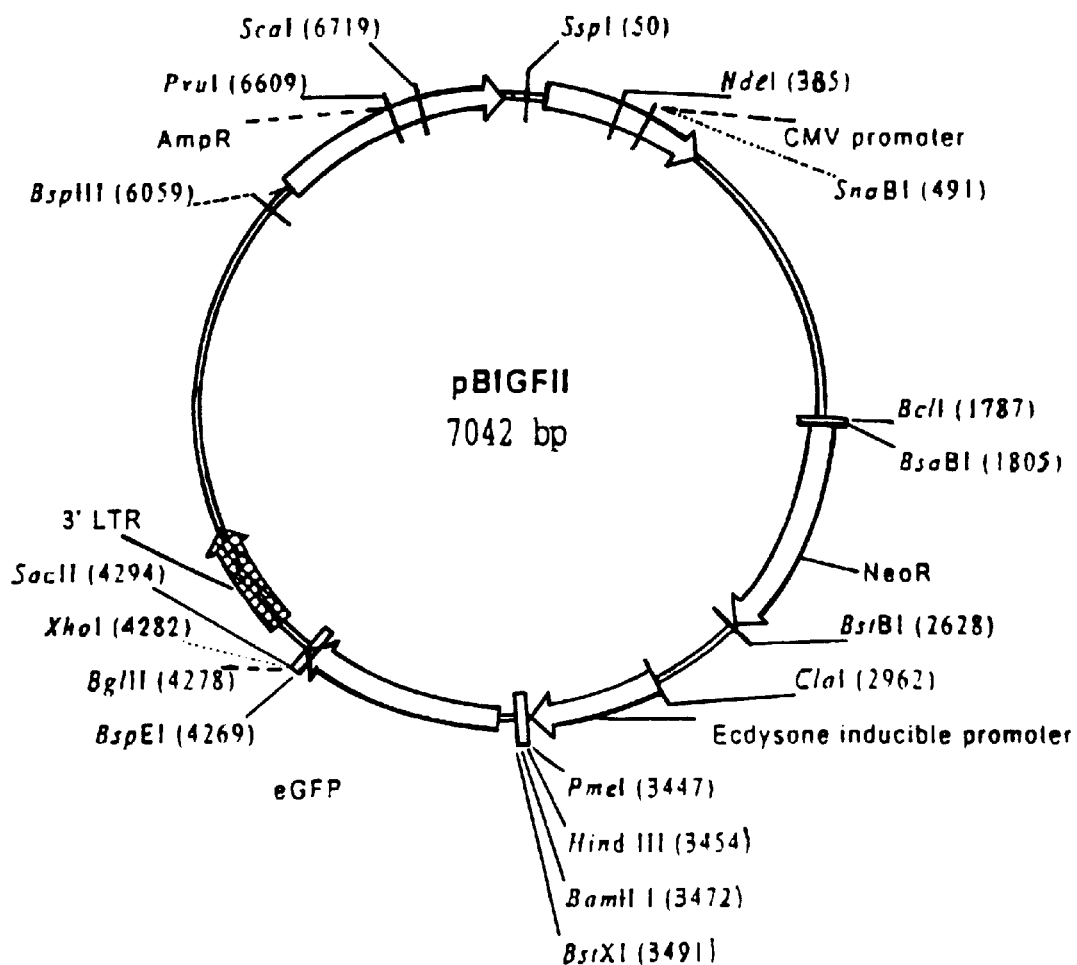

In many MDR cell lines, the drug resistant phenotype has been associated with over-expression of P-glycoprotein (MDR1), a cytoplasmic membrane associated protein that is capable of removing (or pumping) a wide variety of chemotherapeutic drugs from the cell cytoplasm to the extracellular space To enrich for agents that disrupt the pumping action of P-glycoprotein, MDR1 strains are infected with libraries encoding putative and grown in sublethal concentrations of taxol. These cultures are then exposed to Rhodamine 123 (Rh123), a membrane-permeable, fluorescent substrate of P-glycoprotein. Subsequently, floater cells are collected and sorted on the basis of fluorescence. Cells that exhibit a "dim" phenotype by FACS are capable of removing Rh123 from the cytoplasm and thus have an active P-glycoprotein pump (FIG. 17). These cells do not contain an agent that interferes with the P-glycoprotein pump action and are discarded. Cells that are "bright" accumulate Rho123 in the cytoplasmic compartment, and thus contain an agent that disrupts the function of the MDR1 pump. In this Example, the term "disrupts" can refer either to molecules that directly interfere with the action or activation of the MDR1 pump, or to molecules that alter or prevent the localization of P-glycoprotein to its native site. These Rh123 "dim" cells are collected by FACS and recycled through additional rounds of selection (see above) to enrich for sequences that interfere with the pumping action of P-glycoprotein.

As an alternative to this assay, detection of agents that disrupt the action of P-glycoprotein can be performed in the absence of the chemotherapeutic drug. Under these circumstances, cultures of MDR1 cells are infected with a library of inserts encoding putative disruptive agents, cultured for a brief period (24–72 hrs) to allow expression of the library inserts, and treated with trypsin to release the cells from the solid support. The cells are then exposed to Rh123. and sorted by FACS to identify Rh123$^+$ cells (cells that are unable to pump Rh123 out of the cell) within the population. The library insert(s) encoding these agents are then PCR amplified and recycled through additional rounds of selection to enrich for sequences that interfere with the product of the MDR1 gene.

All references cited within the body of the instant specification are hereby incorporated by reference in their entirety.

What is claimed is:

1. A method for performing a selection for cytotoxic agents that cause a lethal phenotype, comprising the steps of:

(a) introducing a genetic library encoding a plurality of putative cytotoxic agents into a population of target cells;

(b) expressing said library in said population of target cells;

(c) plating said population of target cells on a surface;

(d) collecting a subpopulation of target cells that disattaches from said surface within a predetermined period of time; and (e) recovering a first sublibrary from said subpopulation, wherein said subpopulation of cells that disattaches from said surface is enriched for a lethal phenotype that correlates to the presence of said first sublibrary.

2. The method of claim 1, further comprising the step of:

(f) identifying individual cells in said subpopulation that evidence said lethal phenotype.

3. The method of claim 2, wherein said lethal phenotype is apoptosis.

4. The method of claim 2, wherein said lethal phenotype is necrosis.

5. The method of claim 2, wherein said lethal phenotype is growth arrest.

6. The method of claim 1, wherein said sublibrary is at least partially sequenced.

7. The method of claim 1, further comprising the steps of:
 (f) introducing said first sublibrary recovered in step (d) into a second population of target cells;
 (g) plating said second population of target cells on a surface;
 (h) collecting a second subpopulation of target cells that disattaches from said surface; and
 (i) recovering a second sublibrary from said second subpopulation,
 wherein said second subpopulation of cells that disatches from said surface is enriched for a lethal phenotype that correlates to the presence of said second sublibrary.

8. The method of claim 1, wherein said target cells are mammalian cells.

9. The method of claim 8, wherein said mammalian cells are primary cells.

10. The method of claim 9, wherein said primary cells are selected from a group consisting of epithelial cells, endothelial cells, stem cells, mesenchymal cells, fibroblasts, neuronal cells and hematopoietic cells.

11. The method of claim 8, wherein said mammalian cells are cancer cells.

12. The method of claim 1, wherein said cancer cells are derived from solid tumors.

13. The method of claim 11, wherein said cancer cells are metastatic.

14. The method of claim 11, wherein said cancer cells are derived from tissue selected from the group consisting of breast, colon, lung, melanoma and prostate.

15. The method of claim 8 wherein said mammalian cells are genetically altered primary cells.

16. The method of claim 15 wherein said genetically altered primary cell is an immortalized primary cell.

17. The method of claim 15 wherein said genetically altered primary cell is a transformed primary cell.

18. The method of claim 15 wherein said genetically altered primary cell is derived from a primary cell selected from the group consisting of epithelial cells, endothelial cells, stem cells, mesenchymal cells, fibroblasts, neuronal cells and hematopoietic cells.

19. The method of claim 16 wherein said primary cell is immortalized with a gene selected from the group consisting of E6, E7, hTERT, Ras, T-antigen and adenovirus E1a.

20. The method of claim 1 wherein said target cells have a low background of spontaneously disattaching cells.

21. The method of claim 20 wherein said background is no more than about 2%.

22. The method of claim 20 wherein said background is not more than about 10%.

23. The method of claim 20 wherein said target cells are selected from a group consisting of HT29 colon cancer cells, SW620 colon cancer cells, T47D breast cancer cells and HuVEC 8F1868 cells.

24. The method of claim 1, wherein said predetermined period of time is at least about 12 hours.

25. The method of claim 1, wherein said genetic library encodes at least about $1 \times 10^5$ putative cytotoxic agents.

26. A method for obtaining cytotoxic agents that establish a lethal phenotype, comprising the steps of
 (a) providing a population of target cells with a genetic library encoding a plurality of putative cytotoxic agents;
 (b) expressing said library in said population of target cells;
 (c) collecting a subpopulation of cells that display a lethal phenotype; and
 (d) recovering a first sublibrary from said subpopulation;
 wherein said lethal phenotype correlates to the presence of said first sublibrary.

27. The method of claim 26, wherein said lethal phenotype is apoptosis.

28. The method of claim 27, further comprising enriching for said lethal phenotype prior to the step (b) by collecting an enriched subpopulation of cells that disattach from a culturing surface within a predetermined period of time.

29. The method of claim 26, wherein said lethal phenotype is necrosis.

30. The method of claim 26, wherein said lethal phenotype is growth arrest.

* * * * *

UNITED STATES PATENT AND TRADEMARK OFFICE
CERTIFICATE OF CORRECTION

PATENT NO. : 6,582,899 B1
DATED : June 24, 2003
INVENTOR(S) : Carl A. Kamb et al.

It is certified that error appears in the above-identified patent and that said Letters Patent is hereby corrected as shown below:

Column 41,
Line 32, please delete "1" and insert -- 11 --.

Signed and Sealed this

Twenty-third Day of December, 2003

JAMES E. ROGAN
*Director of the United States Patent and Trademark Office*

SEQUENCE LISTING

```
<160> NUMBER OF SEQ ID NOS:  26

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence:
      synthetic - OVT 906
<221> NAME/KEY: misc_feature
<222> LOCATION: (37)..(45)
<223> OTHER INFORMATION: n= a or g or t or c

<400> SEQUENCE: 1
actctggact aggcaggttc agtggccatt atggccnnnn nnnnn            45

<210> SEQ ID NO 2
<211> LENGTH: 42
<212> TYPE: DNA
<213> ORGANISM: Artificial Sequence
<220> FEATURE:
<221> NAME/KEY: misc_feature
<222> LOCATION: (37)..(42)
<223> OTHER INFORMATION: n = a or g or t or c
<223> OTHER INFORMATION: Description of Artificial Sequence:
      synthetic - OVT 908

<400> SEQUENCE: 2
aagcagtggt gtcaacgcag tgaggccgag gcggccnnnn nn               42

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:
      synthetic - OVT 909

<400> SEQUENCE: 3
actctggact aggcaggttc agt                                    23

<210> SEQ ID NO 4
<211> LENGTH: 23
```

```
<212> TYPE: DNA
<213> ORGANISM: Artificial Sequence
<220> FEATURE:
<223> OTHER INFORMATION: Description of Artificial Sequence:
      synthetic - OVT 910

<400> SEQUENCE: 4
aagcagtggt gtcaacgcag tga                                         23

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence:
      synthetic - OVT 312

<400> SEQUENCE: 5
tgagaattcc tcgagttgtt tgtctgccat gatgtatac                        39

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence:
      synthetic - OVT 322

<400> SEQUENCE: 6
tgagaattcg gatccaagaa tggaatcaaa gttaacttc                        39

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:
      synthetic - OVT 329

<400> SEQUENCE: 7
gttagctcac tcattaggca ccc                                         23

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence:
      synthetic - OVT 330

<400> SEQUENCE: 8
cggtatagat ctgtatagtt catccatgcc atgtg                            35

<210> SEQ ID NO 9
<211> LENGTH: 54
<212> TYPE: DNA
<213> ORGANISM: Artificial Sequence
<220> FEATURE:
<221> NAME/KEY: misc_feature
<222> LOCATION: (15)..(43)
<223> OTHER INFORMATION: At the odd numbered nucleotides from
      positions 15 to 43, n= a or g or c or t
<221> NAME/KEY: misc_feature
<222> LOCATION: (16)..(44)
<223> OTHER INFORMATION: At the even numbered nucleotides from
      positions 16 to 44, n= g or c or t
<223> OTHER INFORMATION: Description of Artificial Sequence:
      synthetic - Aptamer  3
```

```
<400> SEQUENCE: 9
tcgagagtgc aggtnnnnnn nnnnnnnnnn nnnnnnnnnn nnnnggagct tctg          54

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence:
      synthetic - Aptamer 4

<400> SEQUENCE: 10
acctgcactc                                                            10

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence:
      synthetic - Aptamer 5

<400> SEQUENCE: 11
gatccagaag ctcc                                                       14

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:
      synthetic - OVT 131

<400> SEQUENCE: 12
gaccttcggc gtccagtgct tcag                                            24

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:
      synthetic - OVT 179

<400> SEQUENCE: 13
agctagcttg ccaaacctac a                                               21

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:
      synthetic - OVT 800

<400> SEQUENCE: 14
gccgccggga tcactctc                                                   18

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence:
      synthetic - OVT 1211

<400> SEQUENCE: 15
```

```
gctagcttgc caaacctaca ggtgggg                                              27
```

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:
      synthetic - OVT 1136

<400> SEQUENCE: 16

```
ggatcactct cggcatggac gag                                                  23
```

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:
      synthetic - OVT 1137

<400> SEQUENCE: 17

```
atccgcggcc gcggccataa tggcc                                                25
```

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:
      synthetic - OVT 777

<400> SEQUENCE: 18

```
gactgccatg gtgagcaagg gc                                                   22
```

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:
      synthetic - OVT 144

<400> SEQUENCE: 19

```
gccgtcctcg atgttgtggc ggat                                                 24
```

<210> SEQ ID NO 20
<211> LENGTH: 194
<212> TYPE: PRT
<213> ORGANISM: Artificial Sequence
<220> FEATURE:
<223> OTHER INFORMATION: Description of Artificial Sequence:
      synthetic - Sequence of Full Length BID and BID Clones #1
      and #2

<400> SEQUENCE: 20

Met Asp Cys Glu Val Asn Asn Gly Ser Ser Leu Arg Asp Glu Cys Ile
  1               5                  10                  15

Thr Asn Leu Leu Val Phe Gly Phe Leu Gln Ser Cys Ser Asp Asn Ser
                 20                  25                  30

Phe Arg Arg Glu Leu Asp Ala Leu Gly His Glu Leu Pro Val Leu Ala
             35                  40                  45

Pro Gln Trp Glu Gly Asp Glu Leu Gln Thr Asp Gly Asn Arg Ser Ser
         50                  55                  60

His Ser Arg Leu Gly Arg Ile Glu Ala Asp Ser Glu Ser Gln Glu Asp
 65                  70                  75                  80

Ile Ile Arg Asn Ile Ala Arg His Leu Ala Gln Val Gly Asp Ser Met
                 85                  90                  95

Asp Arg Ser Ile Pro Pro Gly Leu Val Asn Gly Leu Ala Leu Gln Leu
            100                 105                 110

Arg Asn Thr Ser Arg Ser Glu Gly Asp Arg Asn Arg Asp Leu Ala Thr
        115                 120                 125

Ala Leu Glu Gln Leu Leu Gln Ala Tyr Pro Arg Asp Met Glu Lys Glu
    130                 135                 140

Lys Thr Met Leu Val Leu Ala Leu Leu Ala Lys Lys Val Ala Ser
145                 150                 155                 160

His Thr Pro Ser Leu Leu Arg Asp Val Phe His Thr Thr Val Asn Phe
                165                 170                 175

Ile Asn Gln Asn Leu Arg Thr Tyr Val Arg Ser Leu Ala Arg Asn Gly
            180                 185                 190

Met Asp

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence:
      synthetic - Clone 0113

<400> SEQUENCE: 21

Pro Gln Leu Leu Arg Gln Ala Arg Ser Pro Ala Phe Ile Tyr
 1               5                  10

<210> SEQ ID NO 22
<211> LENGTH: 76
<212> TYPE: PRT
<213> ORGANISM: Artificial Sequence
<220> FEATURE:
<223> OTHER INFORMATION: Description of Artificial Sequence:
      synthetic - Clone 0195

<400> SEQUENCE: 22

Pro Glu Ile Leu Ser Arg Ser His Leu Leu Ala Gly Gln Thr Leu
 1               5                  10                  15

Ile Gly Val Val Ala Met Val Val Glu Ala Glu Gly Glu Glu Asp Pro
            20                  25                  30

Trp Ala Val Glu Ala Met Glu Val Val Ala Val Val Val Ala Glu
        35                  40                  45

Glu Asp Phe Pro Val Glu Val Val Ala Val Glu Asp Ser Ser Glu Leu
    50                  55                  60

Val Thr Gly Ser Val Leu Ile Pro Pro Val Arg Ile
 65                 70                  75

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence:
      synthetic - Clone 0328
<221> NAME/KEY: SITE
<222> LOCATION: (1)..(2)
<223> OTHER INFORMATION: Xaa = unknown

<400> SEQUENCE: 23

```
Xaa Xaa Ala Val Ala Trp Leu Gly Ser Thr Gly Met Thr Cys Gly Ala
 1               5                  10                  15

Gln Arg Leu Arg Ser Leu Arg
            20

<210> SEQ ID NO 24
<211> LENGTH: 106
<212> TYPE: PRT
<213> ORGANISM: Artificial Sequence
<220> FEATURE:
<223> OTHER INFORMATION: Description of Artificial Sequence:
      synthetic - Clone 0461

<400> SEQUENCE: 24

Pro His Ser Val Pro Ala Pro Ser His Leu Ala Val Arg Val Pro Glu
 1               5                  10                  15

Ala Glu Trp Leu His Pro Ser Pro Ser Pro Ala Ser Asp Leu Trp Leu
            20                  25                  30

Trp Ser Pro Cys Pro Cys Leu His Pro Arg Ala Pro His Pro Pro Gly
        35                  40                  45

Phe Thr Lys Glu Gly Gly Ala Val Cys Ser Ser Cys Thr Gln His Leu
    50                  55                  60

Gly Gln Gly Gly Ala Ala Ala Asp Gly Pro Arg Glu Ala Pro Gly Ala
65                  70                  75                  80

Leu Ser Glu Ser Pro Ala Phe Gln Leu Pro Lys Ala Ala Ser Gly Glu
                85                  90                  95

Cys Gly Lys Ala His Arg Ala Leu Ala Ala
            100                 105

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: synthetic

<400> SEQUENCE: 25

Leu Gln Thr Asp
 1

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence:
      synthetic - BH3 domain

<400> SEQUENCE: 26

Leu Ala Gln Val Gly Asp Ser Met Asp
 1               5
```